US008880185B2

(12) United States Patent
Hastings et al.

(10) Patent No.: US 8,880,185 B2
(45) Date of Patent: *Nov. 4, 2014

(54) RENAL DENERVATION AND STIMULATION EMPLOYING WIRELESS VASCULAR ENERGY TRANSFER ARRANGEMENT

(71) Applicant: Boston Scientific Scimed, Inc., Maple Grove, MN (US)

(72) Inventors: Roger N. Hastings, Maple Grove, MN (US); Anthony C. Vrba, Maple Grove, MN (US); Clara Davis, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/926,935

(22) Filed: Jun. 25, 2013

(65) Prior Publication Data

US 2013/0274735 A1 Oct. 17, 2013

Related U.S. Application Data

(63) Continuation of application No. 13/157,844, filed on Jun. 10, 2011, now Pat. No. 8,473,067.

(60) Provisional application No. 61/353,853, filed on Jun. 11, 2010.

(51) Int. Cl.
*A61N 1/00* (2006.01)
*A61B 18/14* (2006.01)
(Continued)

(52) U.S. Cl.
CPC ... *A61B 18/1206* (2013.01); *A61B 2018/00404* (2013.01); *A61B 2018/00023* (2013.01); *A61B 5/04001* (2013.01); *A61B 18/1492* (2013.01); *A61B 2019/5466* (2013.01); *A61F 2250/0001* (2013.01); *A61B 2018/00047* (2013.01); *A61B 2018/167* (2013.01); *A61F 2/82* (2013.01); *A61B 2018/00875* (2013.01); *A61B 5/0538* (2013.01); *A61B 2018/00577* (2013.01); *A61N 1/36125* (2013.01); *A61B 2018/00791* (2013.01); *A61B 2018/00434* (2013.01)
USPC .......................................................... 607/61

(58) Field of Classification Search
USPC .......................................................... 607/61
See application file for complete search history.

(56) References Cited

U.S. PATENT DOCUMENTS

| 164,184 A | 6/1875 | Kidder |
| 1,167,014 A | 1/1916 | O'Brien |

(Continued)

FOREIGN PATENT DOCUMENTS

| DE | 10038737 A1 | 2/2002 |
| EP | 1053720 A1 | 11/2000 |

(Continued)

OTHER PUBLICATIONS

Van Den Berg, "Light echoes image the human body," OLE, Oct. 2001, p. 35-37.

(Continued)

*Primary Examiner* — Robert N Wieland
(74) *Attorney, Agent, or Firm* — Seager, Tufte & Wickhem, LLC

(57) ABSTRACT

Devices, systems, and methods provide for intravascular or extravascular delivery of renal denervation therapy and/or renal control stimulation therapy. Wireless vascular thermal transfer apparatuses and methods provide for one or both of production of current densities sufficient to ablate renal nerves and terminate renal sympathetic nerve activity, and production of current densities sufficient to induce endothelium dependent vasodilation of the renal artery bed. A common apparatus may be used for both renal ablation and control of renal function locally after renal denervation.

20 Claims, 15 Drawing Sheets

(51) Int. Cl.
  *A61B 18/12* (2006.01)
  *A61F 2/82* (2013.01)
  *A61N 1/36* (2006.01)
  *A61B 18/00* (2006.01)
  *A61B 5/04* (2006.01)
  *A61B 19/00* (2006.01)
  *A61B 18/16* (2006.01)
  *A61B 5/053* (2006.01)

(56) References Cited

U.S. PATENT DOCUMENTS

| | | | |
|---|---|---|---|
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,295,484 A | 3/1994 | Marcus et al. |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |

(56) References Cited

U.S. PATENT DOCUMENTS

| | | |
|---|---|---|
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |

(56) References Cited

U.S. PATENT DOCUMENTS

| | | |
|---|---|---|
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |

(56) References Cited

U.S. PATENT DOCUMENTS

| | | |
|---|---|---|
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |

(56) References Cited

U.S. PATENT DOCUMENTS

| | | | |
|---|---|---|---|
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |

(56) References Cited

U.S. PATENT DOCUMENTS

| | | | |
|---|---|---|---|
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Christian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |

(56) References Cited

U.S. PATENT DOCUMENTS

| | | |
|---|---|---|
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,873,471 B2 | 1/2011 | Gieseke |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,398,630 | 3/2013 | Demarais et al. |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0065317 A1 | 4/2003 | Rudie et al. |
| 2003/0092995 A1 | 5/2003 | Thompson |
| 2003/0125721 A1 | 7/2003 | Yon et al. |
| 2003/0139689 A1 | 7/2003 | Shturman et al. |
| 2003/0155539 A1 | 8/2003 | Ginggen |
| 2003/0195501 A1 | 10/2003 | Sherman et al. |
| 2003/0199747 A1 | 10/2003 | Michlitsch et al. |

(56) References Cited

U.S. PATENT DOCUMENTS

| | | |
|---|---|---|
| 2003/0225442 A1 | 12/2003 | Saadat |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147914 A1 | 7/2004 | Kramer |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0055073 A1 | 3/2005 | Weber |
| 2005/0080374 A1 | 4/2005 | Esch et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0256521 A1 | 11/2005 | Kozel |
| 2005/0267556 A1 | 12/2005 | Shuros et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0041277 A1 | 2/2006 | Deem et al. |
| 2006/0062786 A1 | 3/2006 | Salcedo et al. |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184089 A1 | 8/2006 | Makower et al. |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043338 A1 | 2/2007 | Moll et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0173899 A1 | 7/2007 | Levin et al. |
| 2007/0179496 A1 | 8/2007 | Swoyer et al. |
| 2007/0197896 A1 | 8/2007 | Moll et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0250050 A1 | 10/2007 | Lafontaine |
| 2007/0254833 A1 | 11/2007 | Hunter et al. |
| 2007/0260281 A1 | 11/2007 | Hastings et al. |
| 2007/0265687 A1 | 11/2007 | Deem et al. |
| 2007/0276461 A1 | 11/2007 | Andreas et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |

(56) References Cited

U.S. PATENT DOCUMENTS

| | | |
|---|---|---|
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0058836 A1 | 3/2008 | Moll et al. |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097299 A1 | 4/2008 | Andreas et al. |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036873 A1 | 2/2009 | Nielsen et al. |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0182360 A1 | 7/2009 | Makower |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174169 A1 | 7/2010 | Razavi |
| 2010/0174170 A1 | 7/2010 | Razavi |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |

(56) References Cited

U.S. PATENT DOCUMENTS

| | | |
|---|---|---|
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramaniam et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 9962413 A1 | 12/1999 |
| WO | 0047118 A1 | 8/2000 |
| WO | 03026525 A1 | 4/2003 |
| WO | 2004100813 A2 | 11/2004 |
| WO | 2004110258 A2 | 12/2004 |
| WO | 2006022790 A1 | 3/2006 |
| WO | 2006041881 A2 | 4/2006 |
| WO | 2006105121 A2 | 10/2006 |
| WO | 2007035537 A2 | 3/2007 |
| WO | 2007086965 A2 | 8/2007 |
| WO | 2007103879 A2 | 9/2007 |
| WO | 2007146834 A2 | 12/2007 |

(56) References Cited

FOREIGN PATENT DOCUMENTS

| WO | 2008014465 A2 | 1/2008 |
| --- | --- | --- |
| WO | 2007121309 A3 | 3/2008 |
| WO | 2008061152 A2 | 5/2008 |
| WO | 2008070413 A2 | 6/2008 |
| WO | 2007078997 A3 | 10/2008 |
| WO | 2008061150 A3 | 11/2008 |
| WO | 2007103881 A3 | 12/2008 |
| WO | 2008003058 A8 | 7/2009 |
| WO | 2009121017 A1 | 10/2009 |
| WO | 2010067360 A2 | 6/2010 |
| WO | 2010078175 A1 | 7/2010 |
| WO | 2010102310 A2 | 9/2010 |
| WO | 2010129661 A1 | 11/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | 2011130005 A2 | 10/2011 |
| WO | 2011130534 A2 | 10/2011 |
| WO | 2011139589 A2 | 11/2011 |
| WO | 2012019156 A1 | 2/2012 |
| WO | 2013049601 A2 | 4/2013 |

OTHER PUBLICATIONS

"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Products —Functional Measurement," Volcano Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries in Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, Vol. 51, No. 4.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, Vol. 100.

(56) References Cited

OTHER PUBLICATIONS

Tepe et al., "Local Delivery of Paclitaxel to Inhibit Restenosis during Angioplasty of the Leg," The New England Journal of Medicine, 2008, p. 689-699, vol. 358.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Zhou et al., "Mechanism Research of Cryoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).

G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
Stevenson, "Irrigated RF Ablation: Power Titration and Fluid Monagement for Optimal Safety Efficacy," 2005, 4 pages.
Gabriel, "Appendix C: Modeling the frequency dependence of the dielectric properties to a 4 dispersions spectrum," p. 1-49, Nov. 6, 1997.
Han et al., "Third-Generation Cryosurgery for Primary and Recurrent Prostate Caner," BJU International, vol. 93, pp. 14-18, 2004.
Omura et al., "A Mild Acute Compression Induces Neurapraxia in Rat Sciatic Nerve," The International Journal of Neuroscience, vol. 114 (12), pp. 1561-1572, Dec. 2004.
Popma et al., "Percutaneous Coronary and Valvular Intervention," Braunwald's Heart Disease: A Textbook of Cardiovascular Medicine, 7th edition, p. 1364-1405, 2005.
"Optical Coherence Tomography: Advantages of OCT," LightLab Imaging Technology, printed Sep. 3, 2003.
"Optical Coherence Tomography: Image Gallery Cardiovascular Procedures," LightLab Imaging Technology, printed Sep. 3, 2003.
"Optical Coherence Tomography: What is OCT?," LightLab Imaging Technology, printed Sep. 3, 2003.
"Optical Coherence Tomography: Why Use OCT?," LightLab Imaging Technology, printed Sep. 3, 2003.

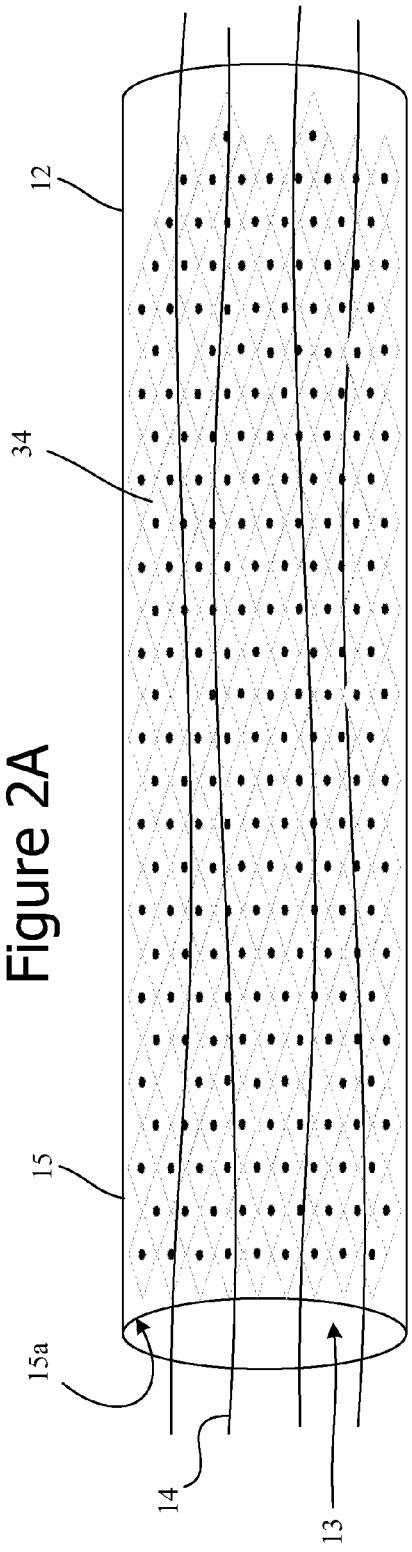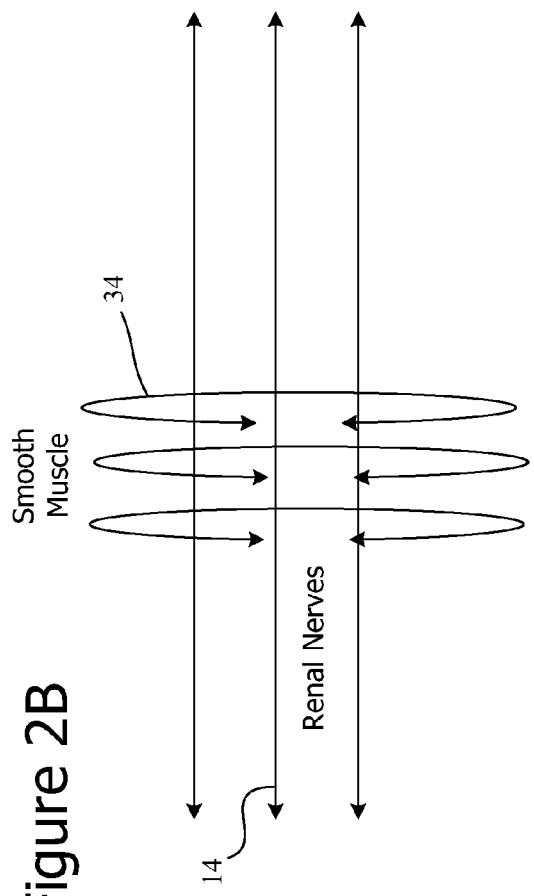
Figure 2A
Figure 2B

RENAL DENERVATION AND STIMULATION EMPLOYING WIRELESS VASCULAR ENERGY TRANSFER ARRANGEMENT

RELATED PATENT DOCUMENTS

The present application is a continuation of U.S. application Ser. No. 13/157,844, filed Jun. 10, 2011, now U.S. Pat. No. 8,473,067, which claims the benefit of Provisional Patent Application Ser. No. 61/353,853 filed on Jun. 11, 2010, to which priority is claimed under 35 U.S.C. §119(e), the entire contents of which are incorporated herein by reference.

TECHNICAL FIELD

The present invention is related to systems and methods for improving cardiac and/or renal function, including renal stimulation and disruption and termination of renal sympathetic nerve activity.

BACKGROUND

The kidneys are instrumental in a number of body processes, including blood filtration, regulation of fluid balance, blood pressure control, electrolyte balance, and hormone production. One primary function of the kidneys is to remove toxins, mineral salts, and water from the blood to form urine. The kidneys receive about 20-25% of cardiac output through the renal arteries that branch left and right from the abdominal aorta, entering each kidney at the concave surface of the kidneys, the renal hilum.

Blood flows into the kidneys through the renal artery and the afferent arteriole, entering the filtration portion of the kidney, the renal corpuscle. The renal corpuscle is composed of the glomerulus, a thicket of capillaries, surrounded by a fluid-filled, cup-like sac called Bowman's capsule. Solutes in the blood are filtered through the very thin capillary walls of the glomerulus due to the pressure gradient that exists between the blood in the capillaries and the fluid in the Bowman's capsule. The pressure gradient is controlled by the contraction or dilation of the arterioles. After filtration occurs, the filtered blood moves through the efferent arteriole and the peritubular capillaries, converging in the interlobular veins, and finally exiting the kidney through the renal vein.

Particles and fluid filtered from the blood move from the Bowman's capsule through a number of tubules to a collecting duct. Urine is formed in the collecting duct and then exits through the ureter and bladder. The tubules are surrounded by the peritubular capillaries (containing the filtered blood). As the filtrate moves through the tubules and toward the collecting duct, nutrients, water, and electrolytes, such as sodium and chloride, are reabsorbed into the blood.

The kidneys are innervated by the renal plexus which emanates primarily from the aorticorenal ganglion. Renal ganglia are formed by the nerves of the renal plexus as the nerves follow along the course of the renal artery and into the kidney. The renal nerves are part of the autonomic nervous system which includes sympathetic and parasympathetic components. The sympathetic nervous system is known to be the system that provides the bodies "fight or flight" response, whereas the parasympathetic nervous system provides the "rest and digest" response. Stimulation of sympathetic nerve activity triggers the sympathetic response which causes the kidneys to increase production of hormones that increase vasoconstriction and fluid retention. This process is referred to as the renin-angiotensin-aldosterone-system (RAAS) response to increased renal sympathetic nerve activity.

In response to a reduction in blood volume, the kidneys secrete renin, which stimulates the production of angiotensin. Angiotensin causes blood vessels to constrict, resulting in increased blood pressure, and also stimulates the secretion of the hormone aldosterone from the adrenal cortex. Aldosterone causes the tubules of the kidneys to increase the reabsorption of sodium and water, which increases the volume of fluid in the body and blood pressure.

Congestive heart failure (CHF) is a condition that has been linked to kidney function. CHF occurs when the heart is unable to pump blood effectively throughout the body. When blood flow drops, renal function degrades because of insufficient perfusion of the blood within the renal corpuscles. The decreased blood flow to the kidneys triggers an increase in sympathetic nervous system activity (i.e., the RAAS becomes too active) that causes the kidneys to secrete hormones that increase fluid retention and vasorestriction. Fluid retention and vasorestriction in turn increases the peripheral resistance of the circulatory system, placing an even greater load on the heart, which diminishes blood flow further. If the deterioration in cardiac and renal functioning continues, eventually the body becomes overwhelmed, and an episode of heart failure decompensation occurs, often leading to hospitalization of the patient.

Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves in the kidneys via renal denervation can reduce blood pressure, and may be a viable treatment option for many patients with hypertension who do not respond to conventional drugs.

SUMMARY

Devices, systems, and methods of the present invention are directed to renal denervation. Devices, systems, and methods of the present invention are directed to renal stimulation for renal function modification. Devices, systems, and methods of the present invention are directed to combined renal denervation and renal stimulation using a common implantable apparatus.

Embodiments of the present invention are directed to apparatuses and methods for intravascular or extravascular delivery of a denervation therapy to a renal artery of a patient. Embodiments of the present invention are directed to apparatuses and methods for intravascular or extravascular delivery of renal stimulation therapy to a renal artery of a patient, with or without delivery of denervation therapy.

Embodiments of the invention are directed to apparatuses and methods that stimulate and control the potential of the endothelium layer of the renal artery. Embodiments of the invention are directed to apparatuses and methods that stimulate and control the potential of the internal elastic membrane of the endothelium of the renal artery. Embodiments of the invention are directed to apparatuses and methods for producing current densities sufficient to hyperpolarize endothelium cells and cause production and release of nitric oxide into blood flowing through the renal artery, the amount of released nitric oxide sufficient to cause vasodilation of the renal artery bed. Embodiments of the invention are directed to controlling renal function locally after renal denervation.

Embodiments of the invention are directed to apparatuses and methods that provide for both production of current densities sufficient to ablate renal nerves and terminate renal sympathetic nerve activity, and production of current densities sufficient to induce endothelium dependent vasodilation of the renal artery bed. A common apparatus may be used for both renal ablation and control of renal function locally after renal denervation.

In accordance with embodiments of the invention, an apparatus for intravascular delivery of one or both of denervation and stimulation therapy to a renal artery of a patient includes a stent dimensioned for deployment within the renal artery and adapted for chronic fixation within the renal artery. An electrode arrangement and an antenna arrangement are supported by the stent. The antenna arrangement is configured to receive energy from a power source external of the renal artery. The electrode and antenna arrangements, in a first configuration, are operative to produce current densities sufficient to ablate renal nerves and terminate renal sympathetic nerve activity. In a second configuration, the electrode and antenna arrangements are operative to produce current densities sufficient to induce endothelium dependent vasodilation of the renal artery bed. The power source for at least the second configuration supplies energy to the antenna arrangement other than by way of a percutaneous electrical lead. In some embodiments, the power source for the first configuration supplies energy to the electrode arrangement via a percutaneous lead.

In some embodiments, the electrode and antenna arrangements, in the second configuration, may be operated to produce current densities sufficient to induce endothelium dependent vasodilation of the renal artery bed distal to the stent. In other embodiments, the electrode and antenna arrangements, in the second configuration, are operative to produce current densities sufficient to hyperpolarize endothelium adjacent the stent and cause production and release of nitric oxide into blood flowing past the stent, the amount of released nitric oxide sufficient to cause vasodilation of the renal artery bed distal to the stent.

According to other embodiments, an apparatus for intravascular delivery of denervation therapy to a renal artery of a patient includes a stent dimensioned for deployment within the renal artery and adapted for chronic fixation within the renal artery. An electrode arrangement is supported by the stent and comprises an anode contact arranged to electrically couple to an inner wall of the renal artery and electrically insulated from blood passing through a lumen of the stent. The electrode arrangement includes a cathode contact arranged to electrically coupled with blood passing through the lumen of the stent and electrically insulated from the inner wall of the renal artery. An antenna arrangement is supported by the stent and electrically coupled to the electrode arrangement, the antenna arrangement configured to receive energy from a power source external of the renal artery. The electrode and antenna arrangements are configured to produce current densities sufficient to ablate renal nerves and terminate renal sympathetic nerve activity, and the power source supplies energy to the antenna arrangement other than by way of a percutaneous electrical lead.

In accordance with further embodiments, an apparatus for intravascular delivery of stimulation therapy to a renal artery of a patient includes a stent dimensioned for deployment within the renal artery and adapted for chronic fixation within the renal artery. An electrode arrangement is supported by the stent and comprises an anode contact arranged to electrically couple to an inner wall of the renal artery and electrically insulated from blood passing through a lumen of the stent. A cathode contact is arranged to electrically couple with blood passing through the lumen of the stent and electrically insulated from the inner wall of the renal artery. An antenna arrangement is supported by the stent and electrically coupled to the electrode arrangement, the antenna arrangement configured to receive energy from a power source external of the renal artery. The electrode and antenna arrangements are configured to produce current densities sufficient to induce endothelium dependent vasodilation of the renal artery bed, and the power source supplies energy to the antenna arrangement other than by way of a percutaneous electrical lead.

In some embodiments, the power source comprises a power source external of the patient. In other embodiments, the power source comprises an implantable power source. The power source may comprise an implantable power source configured to wirelessly couple energy to the antenna arrangement.

For example, the power source may include a patient-external power source and an implantable power source. The patient-external power source is configured to couple energy to the implantable power source, and the implantable power source is configured to wirelessly couple energy to the antenna arrangement.

By way of further example, the power source may include a first implantable power source and a second implantable power source. The first implantable power source may be configured to transmit power to the second implantable power source, and the second implantable power source may be configured to wirelessly couple energy to the antenna arrangement.

In some embodiments, the antenna arrangement comprises an inductive coil. In other embodiments, the stent comprises at least two struts, and the antenna arrangement comprises at least the two struts.

Circuitry may be coupled to the antenna and electrode arrangements. The circuitry may be configured to receive current induced in the antenna arrangement and store a charge developed using the induced current. For example, an electronics module may be supported by the stent and coupled to the antenna and electrode arrangements. The electronics module may include rectifier circuitry and a storage capacitor. The rectifier circuitry is configured to receive current induced in the antenna arrangement and the storage capacitor is configured to store a charge developed using current received from the rectifier circuitry.

In accordance with various embodiments, the power source comprises an implantable structure configured for deployment within a renal vein at a renal vein location proximate a location of the stent within the renal artery. A transmitter is supported by the implantable structure within the renal vein and configured to transmit energy to the antenna arrangement of the renal artery stent via a transvascular pathway. The power source may include an implantable extrathoracic power supply and a lead electrically coupling the power supply and the transmitter. The implantable structure may comprise a stent configured for chronic fixation within the renal vein.

In various embodiments, a controller and a sensing circuit are configured for sensing cardiac activity, and the controller and sensing circuit are supported by the stent disposed in the renal artery. The controller is configured to transmit stimulation pulses to the renal artery wall via the electrode arrangement in synchrony with sensed cardiac events. In other embodiments, a controller and a sensing circuit are configured for sensing cardiac activity, and are respectively supported by the implantable structure disposed in the renal vein. The controller is configured to transmit energy pulses to the antenna arrangement of the renal artery stent in synchrony with sensed cardiac events.

In further embodiments, the implantable renal apparatus is configured to deliver repeated renal nerve ablation in response to detection of re-innervation of the renal artery. One or more sensors may be configured for sensing one or more physiologic parameters that facilitate detection of renal sympathetic nerve activity associated with re-innervation of the renal artery.

In other embodiments, the implantable renal apparatus is configured to deliver repeated renal stimulation in response to detection of one or more physiologic parameters influenced or modulated by one or more renal functions. One or more sensors may be configured for sensing the physiologic parameters that facilitate monitoring of one or more renal functions and detection of changes in renal functions that necessitate remedial renal stimulation therapy.

In some embodiments, a portable power source is configured for transport by an ambulatory patient. The portable power source is configured and controlled to couple energy to the stent in accordance with a predetermined renal artery stimulation therapy.

In accordance with various embodiments, an apparatus for delivering denervation therapy to a renal artery of a patient includes a support structure dimensioned for deployment at the renal artery and configured for chronic fixation at the renal artery. A thermal transfer arrangement is supported by the support structure and comprises one or more thermoelectric elements configured to thermally couple to the renal artery and capable of operating in a hyperthermic configuration. Power circuitry is supported by the support structure and coupled to the thermal transfer arrangement. The power circuit comprises a receiver configured to receive energy from a power source external of the renal artery, the power source supplying energy to the receiver other than by a percutaneous lead.

A control circuit is supported by the support structure and coupled to the power circuitry. The control circuit, in the hyperthermic configuration, is configured to coordinate delivery of hyperthermic ablation therapy to ablate renal nerves and terminate renal sympathetic nerve activity. In some embodiments, one or more of the thermoelectric elements are capable of operating in a hypothermic configuration and situated on the thermal transfer arrangement to cool non-targeted tissues of the renal artery.

According to other embodiments, an apparatus for delivering denervation therapy to a renal artery of a patient includes a support structure dimensioned for deployment at the renal artery and configured for chronic fixation at the renal artery. A thermal transfer arrangement is supported by the support structure and comprises one or more thermoelectric elements configured to thermally couple to the renal artery and capable of operating in a hypothermic configuration. Power circuitry is supported by the support structure and coupled to the thermal transfer arrangement. The power circuit comprises a receiver configured to receive energy from a power source external of the renal artery, the power source supplying energy to the receiver other than by a percutaneous lead. A control circuit is supported by the support structure and coupled to the power circuitry. The control circuit, in the hypothermic configuration, is configured to coordinate delivery of hypothermic ablation therapy to freeze renal nerves and terminate renal sympathetic nerve activity.

In accordance with further embodiments, an apparatus for delivering denervation therapy to a renal artery of a patient includes a support structure dimensioned for deployment at the renal artery and configured for chronic fixation at the renal artery. A thermal transfer arrangement is supported by the support structure and comprises one or more thermoelectric elements configured to thermally couple to the renal artery and capable of selectively operating in a hyperthermic configuration and a hypothermic configuration. The one or more thermoelectric elements comprise solid-state thermoelectric elements. For example, the one or more thermoelectric elements comprise Peltier elements.

Power circuitry is supported by the support structure and coupled to the thermal transfer arrangement, the power circuit comprising a receiver configured to receive energy from a power source external of the renal artery. The power source supplies energy to the receiver other than by a percutaneous lead. A control circuit is supported by the support structure and coupled to the power circuitry. The control circuit, in the hypothermic configuration, is operative to coordinate delivery of hypothermic ablation therapy to freeze renal nerves and terminate renal sympathetic nerve activity. The control circuit, in the hyperthermic configuration, is configured to coordinate delivery of hyperthermic therapy to at least heat renal nerves to above freezing.

The control circuit may be configured to deliver a sequence of freeze/thaw therapy cycles. The control circuit, in the hyperthermic configuration, may be configured to coordinate delivery of a hyperthermic ablation therapy to ablate renal nerves and terminate renal sympathetic nerve activity. The control circuit, in a monitoring configuration in which hyperthermic and hypothermic therapy delivery are disabled, may be operative to coordinate monitoring of at least one physiologic parameter that facilitates detection of renal sympathetic nerve activity associated with re-innervation of the renal artery and/or changes in one or more renal functions.

The support structure may be configured for intravascular or extravascular chronic deployment within the renal artery. For example, the implantable structure may comprise a stent. The power source may comprise a patient-external power source, and implantable power source, or a combination of patient-external and implantable power sources.

In some embodiments, the power source may comprise an implantable structure configured for deployment within a renal vein at a renal vein location proximate a location of the support structure within the renal artery. A transmitter is supported by the implantable structure and configured to transmit energy to the receiver via a transvascular pathway.

In other embodiments, the power source comprises an implantable structure configured for deployment within a renal vein at a renal vein location proximate a location of the support structure within the renal artery. A transmitter is supported by the implantable structure and configured to transmit energy to the receiver via a transvascular pathway. The power source further comprises an implantable extrathoracic power supply and a lead electrically coupling the power supply and the transmitter.

According to further embodiments, a controller and a sensing circuit are configured for sensing cardiac activity. The controller and sensing circuit are supported by the support structure. In some embodiments, the controller is configured to control transfer of thermal energy to the renal artery wall via the thermal transfer arrangement in synchrony with sensed cardiac events. In other embodiments, the controller is configured to control transmission of energy pulses to the receiver of the support structure within the renal artery in synchrony with sensed cardiac events.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

DESCRIPTION OF THE DRAWINGS

FIGS. 2A and 2B illustrate sympathetic innervation of the renal artery;

Figure 1:
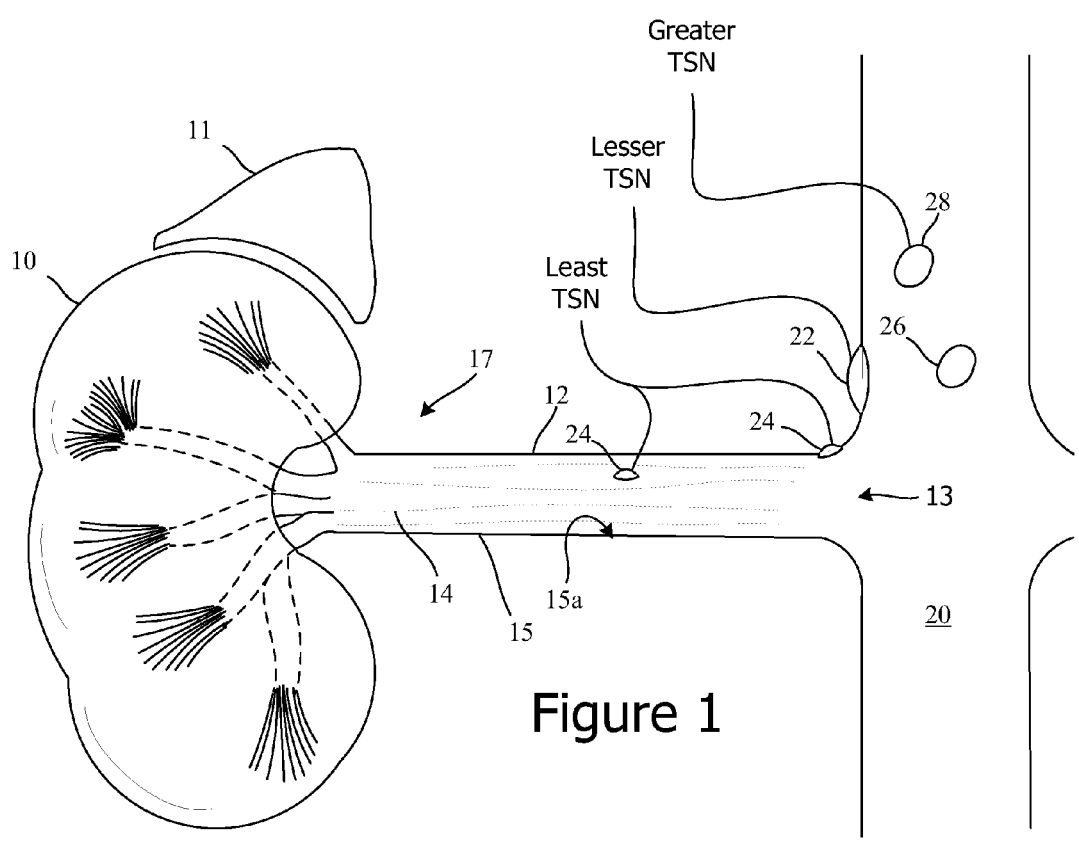
FIG. 1 is an illustration of a right kidney and renal vasculature including a renal artery branching laterally from the abdominal aorta.

While the invention is amenable to various modifications and alternative forms, specifics thereof have been shown by way of example in the drawings and will be described in detail. It is to be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION

In the following description, references are made to the accompanying drawings which illustrate various embodiments of the invention. It is to be understood that other embodiments may be utilized, and structural and functional changes may be made to these embodiments without departing from the scope of the present invention.

Recent human clinical trials have indicated that sympathetic denervation of the kidneys, via ablation of nerve fibers that run along the adventitia of the renal artery, can significantly reduce blood pressure in patients with hypertension that is refractory to drug therapy. It has been hypothesized that this procedure may also be a potent therapy for congestive heart failure, because ablation of the renal nerves reduces sodium reabsorption and reduces production of the enzyme renin by the kidney, in addition to increasing blood flow through the kidney and diuresis via dilation of the renal arteriole bed. However, it is understood that control of vascular function has multiple sources, only one of which being the autonomous nervous system. Local sources of control include nitric oxide (NO) production in the endothelial cells lining the renal artery system, serum carbon dioxide concentration that varies with tissue metabolism, blood pH and temperature.

It is believed that all of these sources have a common effect on the cells in the renal vasculature, namely control of the vascular cell membrane potential. For example, hyperpolarization of smooth muscle (i.e., increase in the magnitude of the membrane potential) causes relaxation and vasodilation, while depolarization of the membrane potential causes vasoconstriction.

Hyperpolarization or depolarization may be accomplished by altering ionic concentrations in the arterial wall extracellular space. For example, injection of negative charge through a pacing electrode cathode depolarizes myocytes and causes a local contraction that propagates throughout the heart. Conversely, reducing blood pH by increased production of carbon dioxide during increased metabolic activity hyperpolarizes neighboring vascular cells and causes smooth muscle cell relaxation and vasodilation, thus providing more blood and oxygen to fuel the increased metabolism.

Local hyperpolarization of endothelial cells propagates down a vascular bed and causes more global vasodilation of the artery bed distal of the local hyperpolarization. This is believed to be due to increased production of NO in the endothelial cells in response to an increase in membrane potential. The NO is carried downstream by the blood flow, resulting in dilation of the distal bed of arterioles. In addition, hyperpolarization may be conducted directly through tight junctions between endothelium cells and through gap junctions to smooth muscle cells.

Embodiments of the invention include a wireless intravascular or extravascular electrode (e.g., a stent electrode) or thermal generator (e.g., stent with thermoelectric elements) placed in or on the renal artery at the time of renal denervation. Stimulation power is preferably transmitted to the stent electrode or thermal generator from a transmit antenna in the adjacent renal vein. The renal vein transmit antenna may be powered using a patient-external device, an implantable medical device via wired or wireless connection, or both power resources. Some embodiments include transvascular implementations with stimulation applied to leads in the renal vein that flows across the vein wall to the nerves adjacent the renal artery. Alternative wireless approaches provide a transmitter in the renal vein that transmits RF power over a short distance to a wireless stent electrode or thermal generator implanted in the renal artery for nerve stimulation or thermal therapy. In some embodiments, renal nerves are ablated, and stimulation current or thermal therapy is thereafter provided to the endothelial cells adjacent the stent to induce endothelium dependent vasodilatation of the renal artery bed to facilitate renal function control and modification.

In some embodiments, an intravascular or extravascular electrode arrangement or thermal generator is configured to provide direct thermal denervation to the renal artery. Various embodiments involve inducing currents in a heating coil and thermally ablating renal artery wall tissue along the length of the heating coil using heat generated in the coil. In other embodiments, the electrode arrangement may be configured to deliver conductive RF heating ablation denervation therapy to the renal artery.

According to some embodiments, an intravascular or extravascular wireless electrode arrangement, such as a stent, is dimensioned for deployment at a proximal renal artery location biased more toward the patient's abdominal aorta than the patient's kidney. Electrode and antenna arrangements of the wireless electrode stent may be configured to produce current densities sufficient to induce endothelium dependent vasodilation of the renal artery bed distal to the stent. For example, the electrode and antenna arrangements of the wireless electrode stent may be configured to produce current densities sufficient to hyperpolarize endothelium adjacent the stent and cause production and release of nitric oxide into blood flowing past the stent. The amount of released nitric oxide is preferably sufficient to cause vasodilation of the renal artery bed distal to the stent.

Apparatuses according to embodiments of the invention may be configured to deliver repeated renal nerve ablation in response to detection of renal nerve regeneration or re-innervation. A sensor may be configured for sensing a physiologic parameter that facilitates detection of renal sympathetic nerve activity associated with renal nerve re-innervation. Repeated renal nerve ablation may be performed based on the sensed physiologic parameter, such as on an ambulatory basis using a portable power source configured and controlled to couple energy to the wireless electrode stent in accordance with a predetermined renal artery stimulation therapy.

The following description with regard to FIGS. 1-3C provides anatomical context for embodiments of the invention that are directed to methods and apparatuses for implementing renal denervation and/or renal stimulation, it being understood that various embodiments may be implemented for deployment and/or treatment for other organs and structures of the body. FIG. 1 is an illustration of a right kidney 10 and renal vasculature including a renal artery 12 branching laterally from the abdominal aorta 20. In FIG. 1, only the right kidney 10 is shown for purposes of simplicity of explanation, but reference will be made herein to both right and left kidneys and associated renal vasculature and nervous system structures, all of which are contemplated within the context of embodiments of the present invention. The renal artery 12 is purposefully shown to be disproportionately larger than the right kidney 10 and abdominal aorta 20 in order to facilitate discussion of various features and embodiments of the present disclosure.

The right and left kidneys are supplied with blood from the right and left renal arteries that branch from respective right and left lateral surfaces of the abdominal aorta 20. Each of the right and left renal arteries is directed across the crus of the diaphragm, so as to form nearly a right angle with the abdominal aorta 20. The right and left renal arteries extend generally from the abdominal aorta 20 to respective renal sinuses proximate the hilum 17 of the kidneys, and branch into segmental arteries and then interlobular arteries within the kidney 10. The interlobular arteries radiate outward, penetrating the renal capsule and extending through the renal columns between the renal pyramids. Typically, the kidneys receive about 20% of total cardiac output which, for normal persons, represents about 1200 mL of blood flow through the kidneys per minute.

The primary function of the kidneys is to maintain water and electrolyte balance for the body by controlling the production and concentration of urine. In producing urine, the kidneys excrete wastes such as urea and ammonium. The kidneys also control reabsorption of glucose and amino acids, and are important in the production of hormones including vitamin D, renin and erythropoietin.

An important secondary function of the kidneys is to control metabolic homeostasis of the body. Controlling hemostatic functions include regulating electrolytes, acid-base balance, and blood pressure. For example, the kidneys are responsible for regulating blood volume and pressure by adjusting volume of water lost in the urine and releasing erythropoietin and renin, for example. The kidneys also regulate plasma ion concentrations (e.g., sodium, potassium, chloride ions, and calcium ion levels) by controlling the quantities lost in the urine and the synthesis of calcitrol. Other hemostatic functions controlled by the kidneys include stabilizing blood pH by controlling loss of hydrogen and bicarbonate ions in the urine, conserving valuable nutrients by preventing their excretion, and assisting the liver with detoxification.

Also shown in FIG. 1 is the right suprarenal gland 11, commonly referred to as the right adrenal gland. The suprarenal gland 11 is a star-shaped endocrine gland that rests on top of the kidney 10. The primary function of the suprarenal glands (left and right) is to regulate the stress response of the body through the synthesis of corticosteroids and catecholamines, including cortisol and adrenaline (epinephrine), respectively. Encompassing the kidneys 10, suprarenal glands 11, renal vessels 12, and adjacent perirenal fat is the renal fascia, e.g., Gerota's fascia, (not shown), which is a fascial pouch derived from extraperitoneal connective tissue.

The autonomic nervous system of the body controls involuntary actions of the smooth muscles in blood vessels, the digestive system, heart, and glands. The autonomic nervous system is divided into the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

In the autonomic nervous system, fibers originating from the central nervous system and extending to the various ganglia are referred to as preganglionic fibers, while those extending from the ganglia to the effector organ are referred to as postganglionic fibers. Activation of the sympathetic nervous system is effected through the release of adrenaline (epinephrine) and to a lesser extent norepinephrine from the suprarenal glands 11. This release of adrenaline is triggered by the neurotransmitter acetylcholine released from preganglionic sympathetic nerves.

The kidneys and ureters (not shown) are innervated by the renal nerves 14. FIGS. 1 and 2A-2B illustrate sympathetic innervation of the renal vasculature, primarily innervation of the renal artery 12. The primary functions of sympathetic innervation of the renal vasculature include regulation of renal blood flow and pressure, stimulation of renin release, and direct stimulation of water and sodium ion reabsorption.

Most of the nerves innervating the renal vasculature are sympathetic postganglionic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Other renal ganglia, such as the renal ganglia 24, superior mesenteric ganglion 26, the left and right aorticorenal ganglia 22, and celiac ganglia 28 also innervate the renal vasculature. The celiac ganglion 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

With particular reference to FIG. 2A, the renal artery 12, as with most arteries and arterioles, is lined with smooth muscle 34 that controls the diameter of the renal artery lumen 13. Smooth muscle, in general, is an involuntary non-striated muscle found within the media layer of large and small arteries and veins, as well as various organs. The glomeruli of the kidneys, for example, contain a smooth muscle-like cell called the mesangial cell. Smooth muscle is fundamentally different from skeletal muscle and cardiac muscle in terms of structure, function, excitation-contraction coupling, and mechanism of contraction.

Smooth muscle cells can be stimulated to contract or relax by the autonomic nervous system, but can also react on stimuli from neighboring cells and in response to hormones and blood borne electrolytes and agents (e.g., vasodilators or vasoconstrictors). Specialized smooth muscle cells within the afferent arteriole of the juxtaglomerular apparatus of kidney 10, for example, produces renin which activates the angiotension II system.

The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14, as is depicted in FIG. 2B.

The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Conversely, increased parasympathetic activity tends to relax the smooth muscle 34, while decreased parasympathetic activity tends to cause smooth muscle contraction.

Figure 3A:
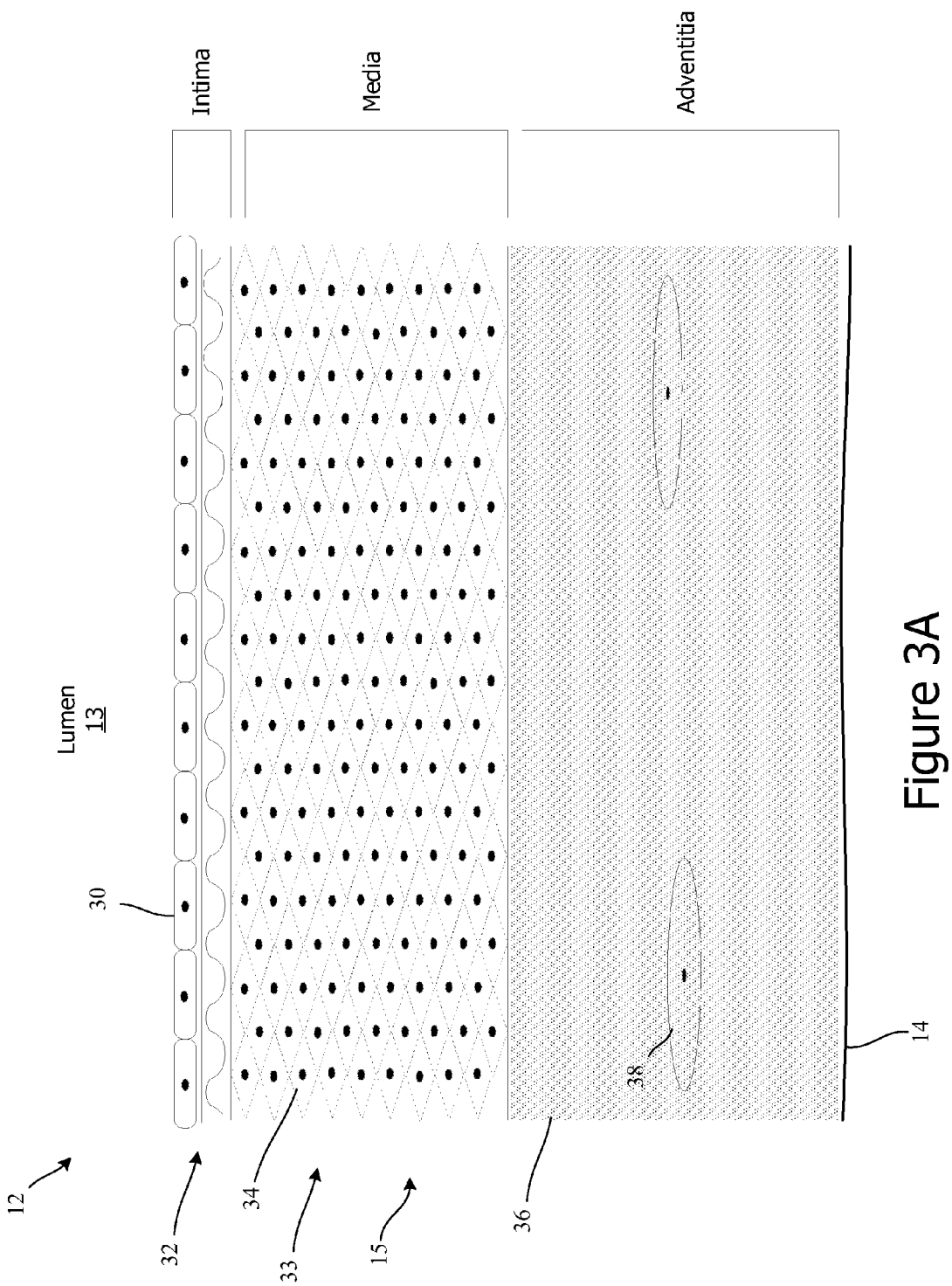
FIG. 3A illustrates various tissue layers of the wall of the renal artery.
Figure 3B:
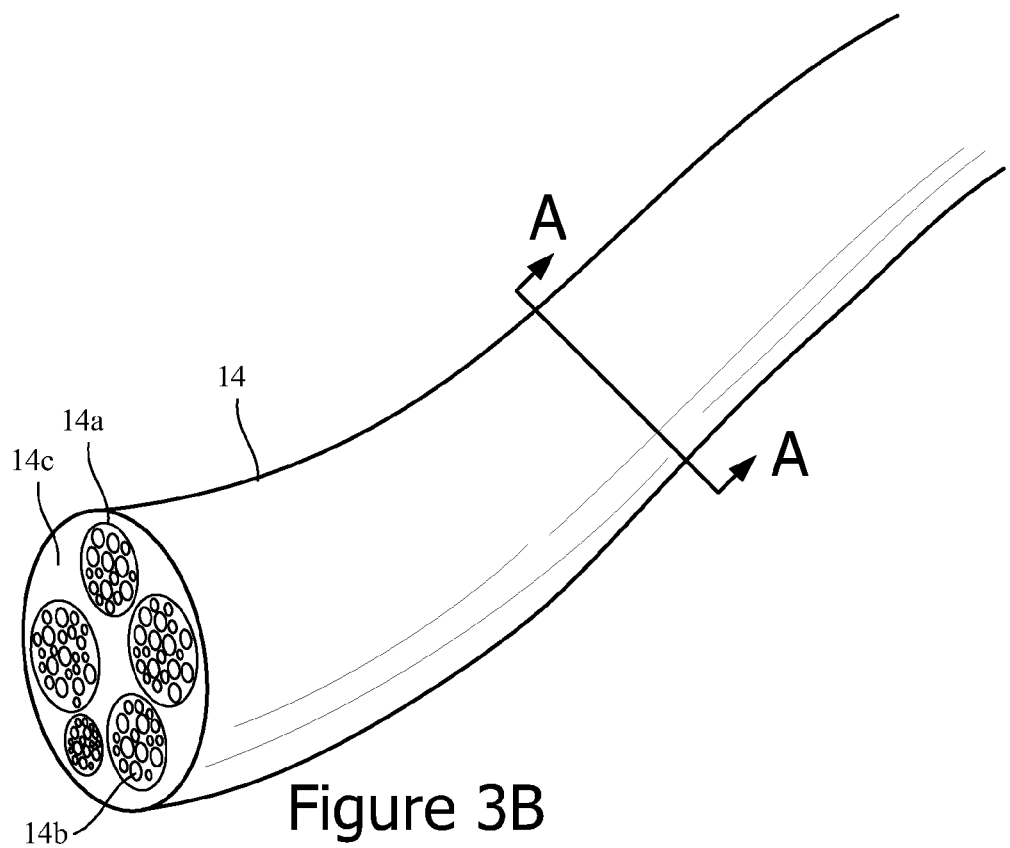
FIGS. 3B and 3C illustrate a portion of a renal nerve.
Figure 3C:
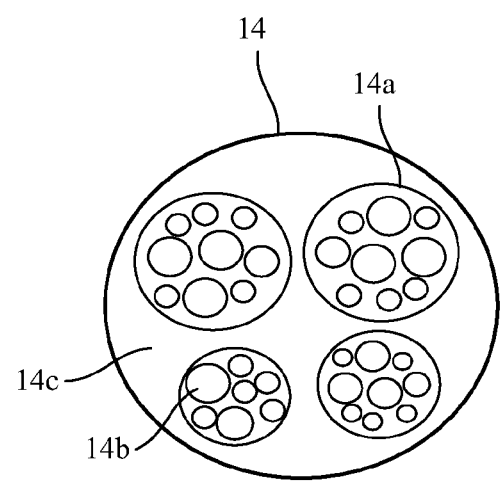

FIG. 3A shows a segment of a longitudinal cross-section through a renal artery, and illustrates various tissue layers of the wall 15 of the renal artery 12. The innermost layer of the renal artery 12 is the endothelium 30, which is the innermost layer of the intima 32 and is supported by an internal elastic membrane. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, such as the membrane of the intima 32 separating the intima 32 from the media 34, and the adventitia 36. The membrane or maceration of the intima 32 is a fine, transparent, colorless structure which is highly elastic, and commonly has a longitudinal corrugated pattern.

Adjacent the intima 32 is the media 33, which is the middle layer of the renal artery 12. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is made up of connective tissue. The adventitia 36 includes fibroblast cells 38 that play an important role in wound healing.

A renal nerve 14 is shown proximate the adventitia 36 and extending longitudinally along the renal artery 12. The main trunk of the renal nerves 14 generally lies at or adjacent the adventitia of the renal artery 12, with certain branches coursing into the media to enervate the renal artery smooth muscle. For example, renal nerves may be situated in the adventitia proximate the outer wall of the renal artery (e.g., tunica adventitia) or within the vasa vasorum, such as the vasa vasorum externae.

A variety of conventional renal denervation approaches have been developed to treat refractory hypertension and heart failure. However, renal functions are only partially controlled by the autonomic nervous system, to which conventional renal denervation approaches are directed. Local factors such as pH, serum carbon dioxide concentration, certain chemicals such as nitric oxide (NO) and temperature further regulate renal function and vascular tone, even after the renal nerves have been ablated.

Embodiments of the invention are directed to apparatuses and methods that stimulate and control the potential of the endothelium layer of the renal artery. Embodiments of the invention are directed to apparatuses and methods that stimulate and control the potential of the internal elastic membrane of the endothelium of the renal artery. Embodiments of the invention are directed to apparatuses and methods for producing current densities sufficient to hyperpolarize endothelium cells and cause production and release of nitric oxide into blood flowing through the renal artery, the amount of released nitric oxide sufficient to cause vasodilation of the renal artery bed. Embodiments of the invention are directed to apparatuses and methods that provide for both production of current densities sufficient to ablate renal nerves and terminate renal sympathetic nerve activity, and production of current densities sufficient to induce endothelium dependent vasodilation of the renal artery bed. The apparatus used for renal ablation may also be used to control renal function locally after renal denervation in accordance with embodiments of the invention.

Embodiments of the invention are directed to apparatuses and methods that stimulate and control local vascular tone via temperature control of renal vasculature. Embodiments of the invention are directed to apparatuses and methods that provide for excitation of renal nerves with a temperature gradient, such as a temperature gradient produced from the hot and cold ends of a Peltier device. Use of a Peltier device in this context advantageously provides for a low energy requirement. In accordance with some embodiments, renal nerves can be stimulated via a temperature gradient generated using infrared light delivered to the renal artery using an intra- or extravascular device.

Figure 4:
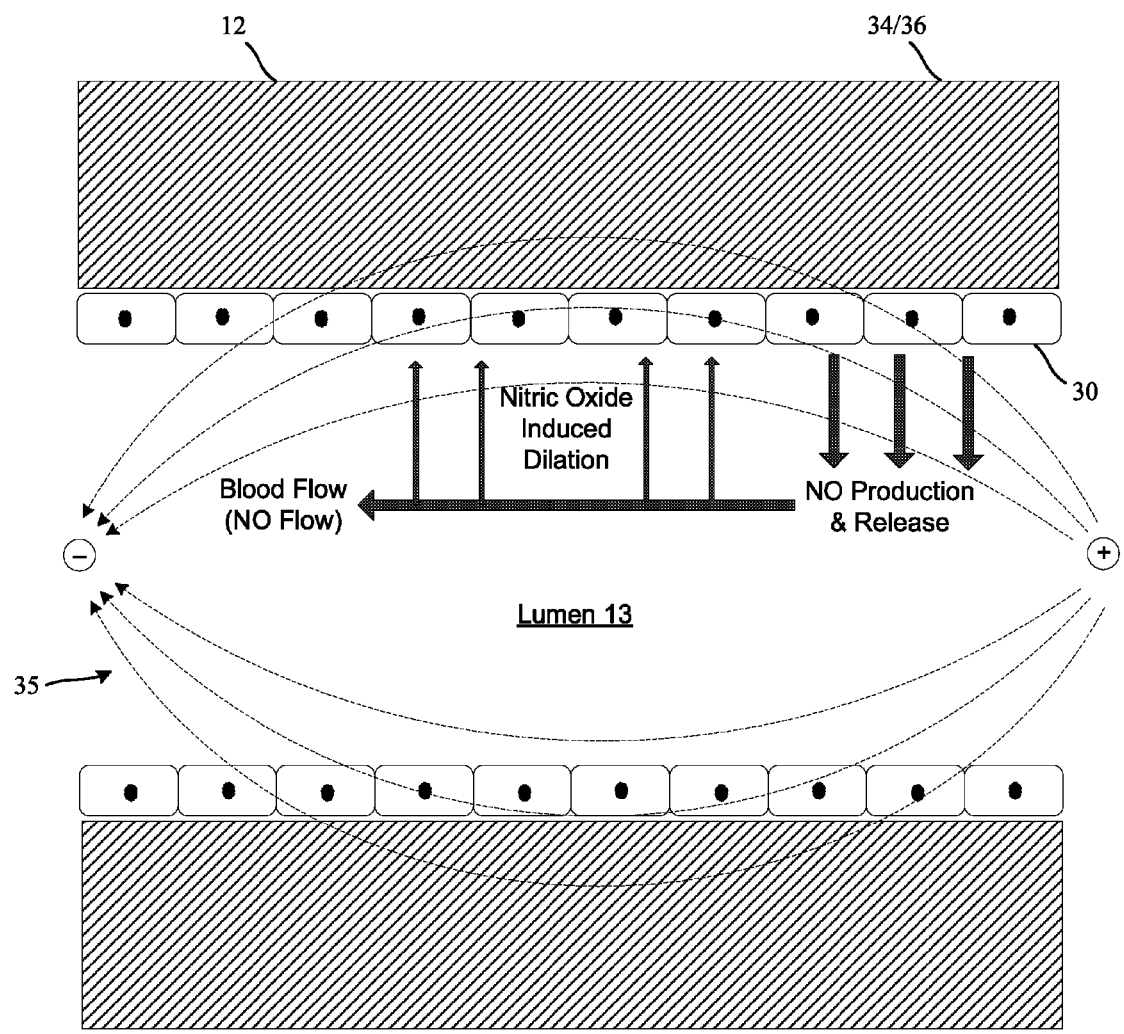
FIG. 4 illustrates a portion of a renal artery shown in cross-section including an electric field superimposed thereon, with electron flow between an anode contact and a cathode contact of an electrode arrangement in accordance with embodiments of the invention.

In FIG. 4, a portion of a patient's renal artery 12 is shown in cross-section with an electric field 35 superimposed thereon, with electron flow between an anode contact (+) and a cathode contact (−). The anode and cathode contacts represent respective contacts of an electrode arrangement configured for deployment in the lumen 13 of the renal artery 12. The electrode arrangement is controlled to stimulate and control the membrane potential on endothelium cells adjacent the electrode arrangement. For example, hyperpolarization of the internal elastic membrane of the endothelium 30 of the renal artery induces endothelium dependent vasodilation, which propagates to the distal arteriole bed directly through cell junctions and indirectly through hyperpolarization induced release of nitric oxide into the blood. Control of the electrode arrangement depicted in FIG. 4 provides for local control of renal function after renal denervation.

FIGS. 5A-6C show various embodiments of an implantable vascular apparatus 50 configured to deliver energy to innervated renal vasculature in accordance with embodiments of the invention. The embodiments shown in FIGS. 5A-6C include apparatuses 50 that provide for renal function control via renal stimulation, such as apparatuses configured to generate and control an electric field to achieve a desired membrane potential on endothelium cells of the renal artery. The embodiments shown in FIGS. 5A-6C include apparatuses for delivering thermal denervation therapy to renal vasculature, such as apparatuses that deliver thermal energy directly to the renal artery wall.

Implantable apparatuses according to the embodiments of FIGS. 5A-6C may be configured for positioning within the renal artery at one or more renal artery lumen locations for purposes of delivering renal denervation therapy, and subsequently implanted at a permanent renal artery lumen location to effect long-term renal function control. Apparatuses according to the embodiments of FIGS. 5A-6C may be chronically implanted at a desired renal artery lumen location for both denervation and renal function control purposes.

Figure 5A:
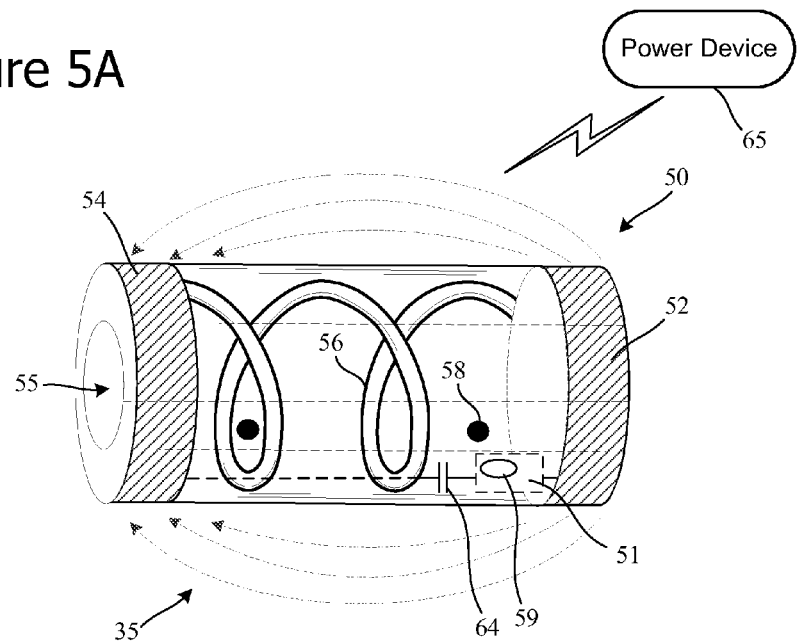
FIG. 5A illustrates an implantable vascular apparatus configured to deliver thermal energy to innervated renal vasculature in accordance with embodiments of the invention.

FIG. 5A illustrates an implantable vascular apparatus 50 configured to deliver thermal energy to innervated renal vasculature in accordance with embodiments of the invention. The implantable vascular apparatus 50 shown in FIG. 5A includes an energy source 56 and a multiplicity of electrodes 52, 54, and is dimensioned for deployment in a renal artery 12 of a patient. The implantable vascular apparatus 50 typically has a generally cylindrical shape with an inner void 55 that provides for renal arterial blood flow therethrough. The electrodes 52, 54 are preferably thermally insulated to prevent or reduce cooling of the electrodes 52, 54 by blood passing through the renal artery.

The energy source 56 for the implantable vascular apparatus 50 is coupled to the electrodes 52, 54. In the embodiment shown in FIG. 5A, the energy source 56 includes an inductive coil or antenna that receives energy from a power device 65 external of the renal artery 12. A capacitor 64 is shown connected in parallel with the coil 65, which can represent a physical component or the self-capacitance of the inductive coil 65. The power device 65 induces an AC current in the coil 56, causing heating at each of the electrodes 52, 54. Ohmic heat is produced by the induced AC current as it passes through resistive tissues of the renal artery wall to renal nerves and ganglia.

The capacitance of the capacitor 64 is preferably selected to tune the inductive coil circuit 56 to the frequency of the power device 65. The external power device 65 may be an RF energy source located outside of the body or within the body, such as within a vessel (e.g., renal vein 42 or the inferior vena cava 40), a body cavity or a subcutaneous pocket. In some embodiments, an electrical lead may be coupled to the implantable vascular apparatus 50 directly. Preferred embodiments include those that employ a separate energy source (in vivo or ex vivo) that wirelessly provides power for the implantable vascular apparatus 50.

Figure 5B:
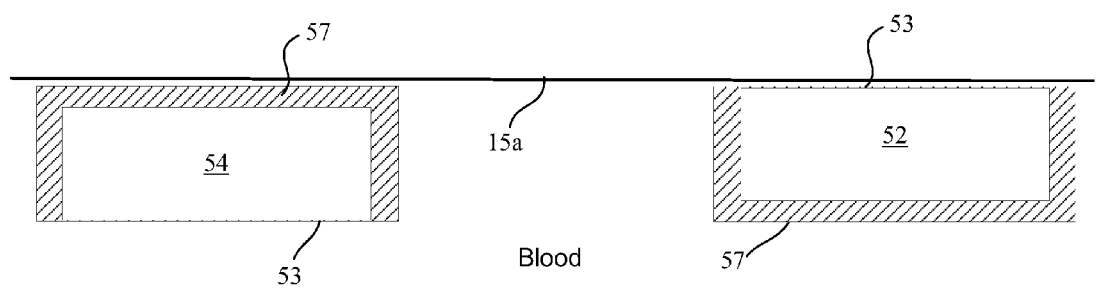
FIG. 5B shows a partial cross-section of an anode contact and a cathode contact of an electrode arrangement situated adjacent an inner wall of the renal artery or other innervated vessel that contributes to renal sympathetic nerve activity or renal function in accordance with embodiments of the invention.

FIG. 5B illustrates an electrode arrangement of an implantable vascular apparatus 50 configured for hyperpolarizing innervated renal vasculature in accordance with embodiments of the invention. The electrode arrangement shown of FIG. 5B may alternatively or additionally be used to deliver direct thermal energy to the renal artery wall via an anode of the electrode arrangement. In this configuration, it is desirable to thermally insulate the back of the anode to prevent or reduce blood cooling, and to electrically insulate the anode from the blood that flows through the vessel. The electrode arrangement shown in FIG. 5B is preferably coupled to an inductive coil or antenna, and may be implemented in an intravascular apparatus of the type generally shown in FIG. 5A or FIG. 6A, for example.

Figure 16:
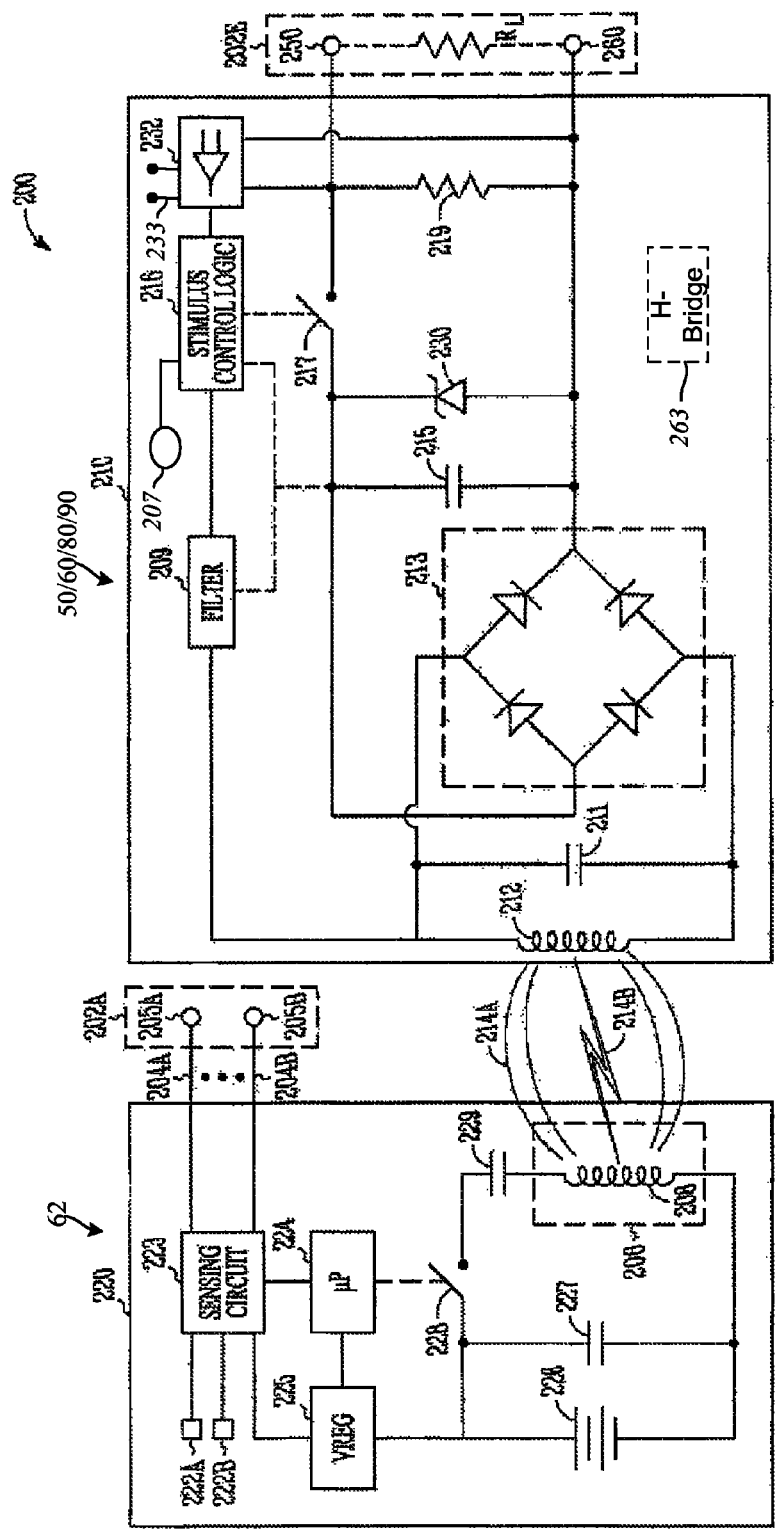
FIG. 16 is a schematic of a renal denervation and/or renal stimulation system in accordance with embodiments of the invention.

In a DC configuration, the electrode arrangement shown in FIG. 5B is coupled to a diode or rectifier that converts AC current induced in the coil or antenna 56 by an RF power device 65 to DC (see, e.g., FIG. 16). In some embodiments, a switch arrangement may be included to facilitate switching of components (e.g., capacitors, diodes, rectifiers) to selectively change the electrode arrangement configuration of the implantable vascular apparatus 50 between AC and DC configurations. Selectively changing electrode arrangement configurations of the implantable vascular apparatus 50 allows for selective delivery of thermal ablation and renal function stimulation (e.g., hyperpolarization) therapies.

FIG. 5B show partial cross-sections of anode contact 52 and cathode contact 54 of the electrode arrangement of FIG. 5A situated adjacent an inner wall 15a of the renal artery or other innervated vessel that contributes to renal sympathetic nerve activity or renal function. In FIG. 5B, the anode contact 52 is shown to include a first region 53 in contact with inner vessel wall tissue 15a and a second region 57 that extends into the lumen 13 of the vessel and is exposed to blood within the vessel. The first electrode region 53 is configured to directly contact the inner vessel wall tissue 15a, and the second electrode region 57 includes insulation that electrically insulates the second electrode region 57 from blood that flows within the vessel. The first electrode region 53 of the anode contact 52 hyperpolarizes the adjacent endothelium 30 and smooth muscle 34 of the vessel wall tissue. It is considered important that the anode contact 52 be insulated from blood flow partly as a means to prevent electro-coagulation of blood at the anode contact 52 of the implantable vascular apparatus 50.

FIG. 5B also shows a cathode contact 54 that includes a first region 53 that extends into the lumen 13 of the vessel and is exposed to blood within the vessel. The first region 53 is configured to electrically couple with the blood within the vessel. The cathode contact 54 includes a second region 57 that includes insulation for electrically insulating the cathode contact 54 from the inner vessel wall tissue 15a. In some configurations, the cathode contact 54 extends into the void 55 of the implantable vascular apparatus 50 and this extension of the cathode contact 54 is free of insulation and exposed to the blood within the vessel. The remaining portion of the cathode contact 54 is either situated out of contact with the inner vessel wall tissue 15a or includes insulation to electrically isolate the cathode contact 54 from the inner vessel wall tissue 15a.

Figure 6A:
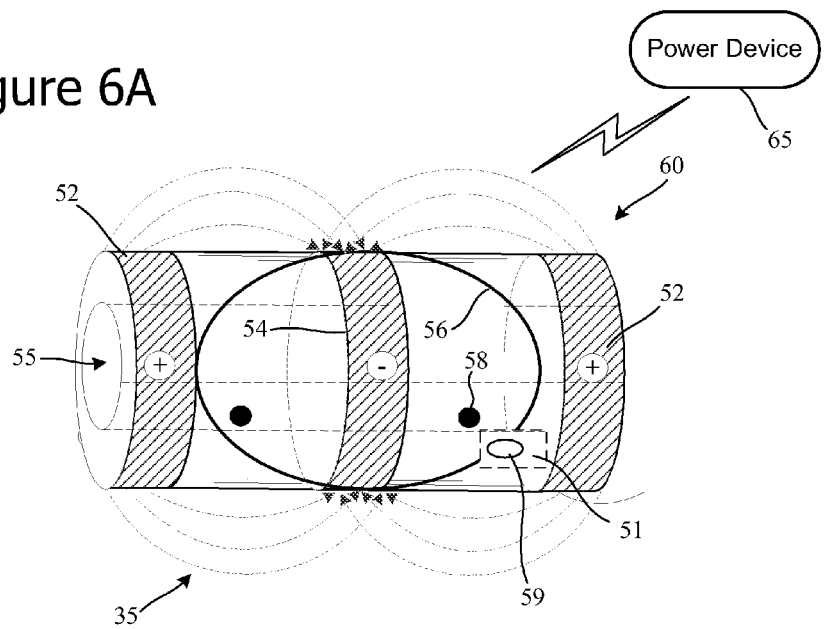
FIG. 6A illustrates an implantable vascular apparatus which includes a multiplicity of anode contacts and a common or shared cathode in accordance with embodiments of the invention.
Figure 6B:
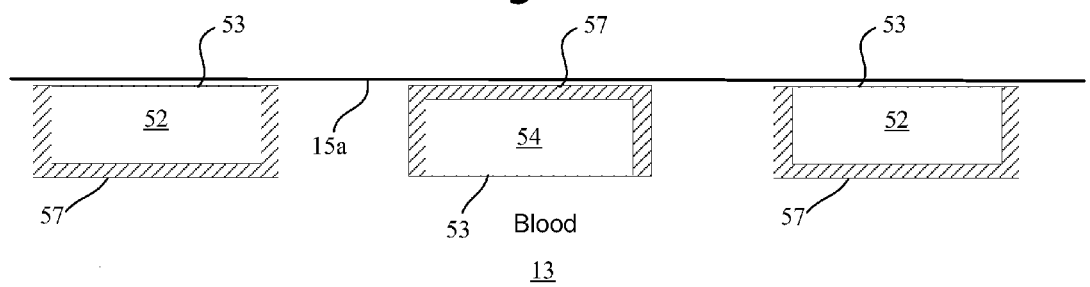
FIG. 6B shows a partial cross-section of the electrode arrangement of FIG. 6A, including two anode contacts and a shared cathode contact in accordance with embodiments of the invention.
Figure 6C:
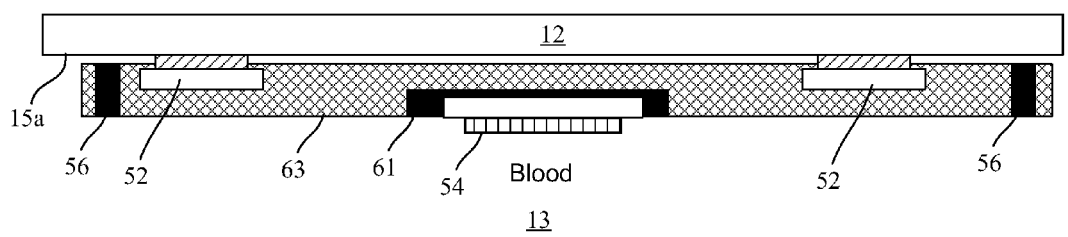
FIG. 6C shows a partial cross-section of two anode contacts and a shared cathode contact of the implantable vascular apparatus of FIG. 6A in accordance with embodiments of the invention.

FIG. 6A illustrates an implantable vascular apparatus 60 in accordance with embodiments of the invention deployed in a renal artery 12 of a patient. The implantable vascular apparatus 60 shown in FIG. 6A includes an energy source 56 and a multiplicity of electrodes 52, 54, and is dimensioned for deployment in a renal artery 12 of a patient. Additional details of the electrodes 52, 54 of the implantable vascular apparatus 60 of FIG. 6A are shown in FIGS. 6B and 6C. The implantable vascular apparatus 60 typically has a generally cylindrical shape with an inner void 55 that provides for renal arterial blood flow therethrough. The implantable vascular apparatus 60 shown in FIG. 6A includes two anode contacts 52 and a single shared cathode contact 54. The two anode contacts 52 are positioned relative to opposing ends of the implantable vascular apparatus 60, respectively, and the cathode contact 54 is positioned at a center location of the implantable vascular apparatus 60.

The energy source 56 for the implantable vascular apparatus 60 is coupled to the anode contacts 52 and the cathode contact 54, and includes an antenna configured to receive energy transmitted from a power device 65 external of the renal artery 12. The antenna 56 may comprise a coil antenna, for example. The external power device 65 may be an RF energy source located outside of the body. Preferably, the external power device 65 is an implantable device that can be positioned within the body, such as within the renal vein 42, the inferior vena cava 40, or a body cavity or subcutaneous pocket.

In some embodiments, the implantable power device 65 is positioned in proximity to the implantable vascular apparatus 60 situated within the renal artery 12 and configured to receive energy from an ex vivo power source, such as an RF generator located in proximity to the patient. The implantable power device 65 may then wirelessly transmit energy to the antenna 56 of the implantable vascular apparatus 60 located within the lumen of the renal artery 12.

In other embodiments, the implantable power device 65 receives energy from an in vivo power source via an implantable electrical lead. The in vivo power source may be a battery of an implantable medical device, such as an implantable stimulator, a cardiac rhythm management device such as a pacemaker, cardiac resynchronizer, implantable cardioverter-defibrillator, or a neurostimulation device. The implantable power device 65 may then wirelessly transmit power to the antenna or coil 56 of the implantable vascular apparatus 60 located within the lumen of the renal artery 12.

FIG. 6B show partial cross-sections of two anode contacts 52 and a cathode contact 54 of the electrode arrangement of FIG. 6A situated adjacent an inner wall 15a of the renal artery or other innervated vessel that contributes to renal sympathetic nerve activity or renal function. The anode contacts 52 and cathode contact 54 shown in FIG. 6B have the same configuration as those illustrated in FIG. 5B discussed hereinabove.

FIG. 6C show partial cross-sections of two anode contacts 52 and a cathode contact 54 of the implantable vascular apparatus 60 of FIG. 6A situated adjacent an inner wall 15a of the renal artery 12 or other innervated vessel that contributes to renal sympathetic nerve activity or renal function in accordance with embodiments of the invention. In the embodiment shown in FIG. 6C, the implantable vascular apparatus 60 comprises a stent 63 which supports the anode contacts 52 and the cathode contact 54. The two anode contacts 52 are situated on the stent 63 so as to directly contact the inner wall 15a of the renal artery 12. The anode contacts 52 may be electrically tied together and coupled to the antenna 56, or may be individually coupled to the antenna 56. It is noted that the stent 63 may support one, two or more antennae 56, and that the antennae 56 may comprise separate elements mounted on the stent 63 or be integral to the stent structure, such as one, two, or more struts of the stent 63. The cathode contact 54 is exposed to the lumen 13 of the renal artery 12 and electrically couples with blood flowing within the artery 12. An insulator 61 is disposed between the cathode contact 54 and the stent body 63 such that the cathode contact 54 is electrically isolated from the inner vessel wall 15a.

The implantable vascular apparatus 50, 60 shown in FIGS. 5A-6C may be operated in one or multiple configurations or modes. According to various embodiments, the implantable vascular apparatus 50, 60 is chronically implanted within the renal artery 12 and operable in a denervation mode. In a denervation mode of operation, the energy source 56 is controlled via an external energy device and/or an electronics module 51 coupled to the energy source 56 to generate ablative energy sufficient to denervate renal nerves and ganglia, such as by inducing electrical currents that heat the renal artery wall to a sufficiently high temperature to kill renal nerves and ganglia (e.g., necrotic coagulation of the innervated renal tissue).

For example, target renal artery tissue can be heated using the implantable vascular apparatus 50, 60, and, if the artery wall tissue temperature exceeds 50° C., the tissue can be killed. However, the target tissue will not be physically and permanently disrupted until the temperature of the target tissue exceeds about 65° C., where the collagen reforms. When the temperature within the target tissue reaches a sufficient level (e.g., >65° C.), the target tissue is thermally coagulated.

In some embodiments, the implantable vascular apparatus 50, 60 is chronically implanted within the renal artery 12 and configured to provide for renal function control via renal stimulation. An electric field 35 is generated across the anode and cathode contact 52, 54 and controlled to achieve a desired membrane potential on endothelium cells 30 adjacent the implantable vascular apparatus 50, 60. The implantable vascular apparatus 50, 60 can be controlled via the external energy device and/or an electronics module 51 coupled to the energy source 56 to control hyperpolarization of the internal elastic membrane of the endothelium 30 and the degree of endothelium dependent vasodilation. According to various embodiments, the implantable vascular apparatus 50, 60 illustrated in FIGS. 5A-6C provides for local control of renal function, which is desirable for patient's who have undergone renal denervation.

In accordance with further embodiments, the implantable vascular apparatus 50, 60 is chronically deployed within the renal artery 12 and configured to deliver renal denervation therapy in a first mode of operation, and used in a second mode of operation to provide renal stimulation therapy for renal function control following renal denervation. The implantable vascular apparatus 50, 60 may be positioned within the renal artery at one or more renal artery lumen locations for purposes of delivering renal denervation therapy to the patient's renal artery 12, and subsequently implanted at a permanent renal artery lumen location. In some embodiments, it may be desirable to chronically implant the implantable vascular apparatus 50, 60 for both denervation and renal function control purposes.

It is desirable to concentrate denervation energy in the tissues of the adventitia 36 and the vaso vasorum that include renal nerves and ganglia, and to reduce the concentration of denervation energy in the tissues of the endothelium 30 and media 34. For example, it is desirable that the renal artery inner wall tissue temperature not exceed 50° C., while the tissues of the adventitia 36 and the vaso vasorum that include renal nerves and ganglia exceed 50° C., preferably exceeding 65° C. or higher. Cooling of the endothelium 30 and tissue of the media 34 near the endothelium 30 can be achieved using a variety of apparatuses and techniques.

For example, cooling of the endothelium 30 and tissue of the media 34 near the endothelium 30 can be achieved by channeling blood flow in the renal artery to locations adjacent the endothelium 30. Local endothelium/medial tissue cooling may be provided using various devices, such as thermoelectric elements (e.g., Peltier devices) or a separate cooling catheter, cooling balloon, cryocatheter or cryoballoon arrangement. For example, a separate cooling arrangement comprising a balloon or cryoballoon can be navigated to the renal artery 12, and positioned within the void 55 of the implantable vascular apparatus 50, 60. The balloon can be inflated with the cooling arrangement positioned within the void 55 to provide local cooling to the endothelium 30 and medial tissue. It is noted that in electrode arrangement embodiments that employ direct heating elements, these elements can be thermally insulated relative to the cooling arrangement so as to maintain efficient thermal transfer of heat between the direct heating elements to the vessel wall.

In some embodiments according to FIGS. 5A-6C, power rectification, conditioning, and/or control electronics is included as part of a power device 65 external to the renal artery 12, and the energy received and delivered by the energy source 56 of the implantable vascular apparatus 50, 60 is entirely or at least mostly controlled by the external power device electronics 65. In other embodiments, at least some of the power rectification, conditioning, and control electronics needed to controllably deliver denervation and renal stimulation energy to renal artery tissue are included as part of an electronics module 51 of the implantable vascular apparatus 50, 60.

For example, and in accordance with various embodiments, a tank circuit of the electronics module 51 or other circuitry may be coupled to the energy source 56 of the implantable vascular apparatus 50, 60 to facilitate rectification and conditioning of received energy and controlled delivery of energy to renal artery tissue. The tank circuit may include a storage capacitor that is charged to a predetermined voltage in response to energy received by the inductive coil 56. The tank circuit or other section of the electronics module 51 may include logic circuitry or a microprocessor that controls voltage and current delivery parameters for one or both of denervation and renal stimulation modes of operation. Control signals for regulating energy reception and delivery parameters may be impressed in the energy source signal generated by the external power device 65 (e.g., an RF signal for wireless energy transfer or an electrical signal for wireline energy transfer), preferably in an encoded format if wirelessly transmitted. It is noted that the tank circuit may alternatively be incorporated in the external power 65 device, and the coil 56 of the implantable vascular apparatus 50, 60 may be configured as an antenna that receives energy from the external power device 65.

The electronics module 51 may include or be coupled to one or more temperature sensors 59 which sense temperature at the implantable vascular apparatus 50, 60 and/or the inner vessel wall of the renal artery 12. Temperature data acquired by the temperature sensor 59 is preferably communicated to the electronics module 51 via a conductor. The electronics module 51 transmits a signal that incorporates the temperature data to a device external of the renal artery 12 via the coil 56 or a separate antenna, preferably in an encoded format. The temperature data is useful for controlling the operation of the implantable vascular apparatus 50, 60, such as by controlling the magnitude and duration of current/heat generation for one or both of renal denervation and renal stimulation procedures. As was discussed previously, the operation of the implantable vascular apparatus 50, 60 can be controlled by the electronics module 51, a device external of the implantable vascular apparatus 50, 60 (e.g., power device 65 or a patient-external device), or a combination of control resources.

Figure 7:
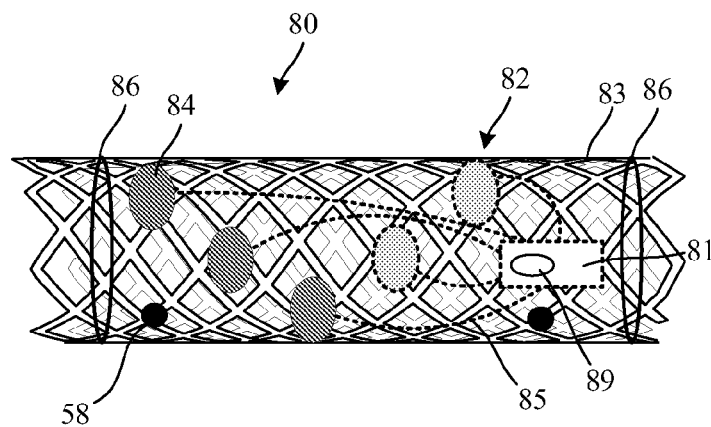
FIGS. 7-9 illustrate embodiments of an implantable intravascular apparatus comprising one or more thermoelectric elements configured to deliver denervation therapy and/or renal stimulation therapy to innervated renal vasculature in accordance with embodiments of the invention.
Figure 8:
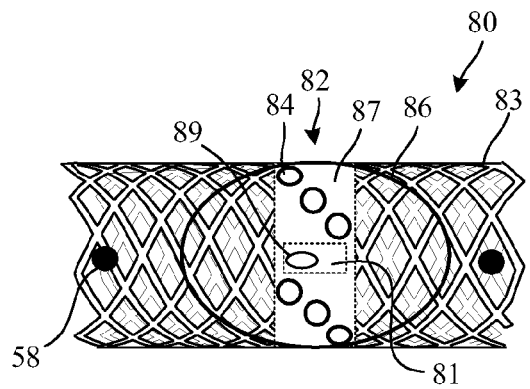
Figure 9:
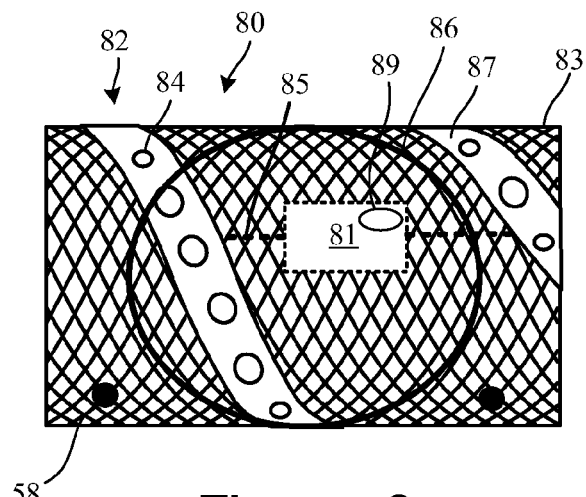

FIGS. 7-9 illustrate embodiments of an implantable vascular apparatus 80 configured to deliver denervation therapy and/or renal stimulation therapy to renal vasculature. The embodiments shown in FIGS. 7-9 includes a support structure 83 dimensioned for deployment at the renal artery 12. The support structure 83 is preferably configured for chronic fixation within the lumen of the renal artery 12, and may be implemented as a stent. A thermal transfer arrangement 82 is supported by the support structure 83 and comprises one or more thermoelectric elements 84 configured to thermally couple to the inner wall of the renal artery 12. The thermoelectric elements 84 preferably comprise solid-state thermoelectric elements, such as Peltier elements. Various Peltier-effect elements and support, connection, and control arrangements and methodologies that can be adapted for use in embodiments of the present invention are disclosed in commonly owned U.S. Pat. No. 7,238,184, which is incorporated herein by reference.

In FIGS. 7-9, the thermal transfer arrangement 82 comprises a number of thermoelectric elements 84 distributed on the surface of the support structure 83 in accordance with a predetermined pattern. In FIG. 7, a number of thermoelectric elements 84 are situated in relative isolation to one another on the surface of the support structure 83 in accordance with a generally spiral or helical pattern.

In FIG. 8, a number of thermoelectric elements 84 are situated on a substrate 87, which is shown to have a generally cylindrical shape that encircles the support structure 83. A number of thermoelectric elements 84 are situated on the substrate 87 in accordance with a generally spiral or helical pattern. The substrate 87 may be formed from a thermally conductive material, a thermally insulating material, or a combination of strategically positioned thermally conductive and thermally insulating material.

In FIG. 9, a number of thermoelectric elements 84 are situated on a substrate 87, which is shown to have a generally spiral that encompasses at least one revolution of the support structure 83. It is noted that some embodiments may employ two or more substrates 87 having a spiral shape that partially or completely encompasses at least one revolution of the support structure 83. The thermoelectric elements 84 of these two or more substrates 87 may be thermally coupled or decoupled from one another by appropriate positioning of thermally conducting and/or insulating material.

In FIGS. 8 and 9, selected ones or sets of the thermoelectric elements 84 may be disposed on thermally conductive and/or thermally insulating portions of the substrate 87. For example, several thermoelectric elements 84 may be disposed on thermally conductive portions of the substrate 87 to provide for increased thermal energy output and/or an increased surface area for generating thermal energy. Selected ones or sets of the thermoelectric elements 84 may be disposed on thermally insulating portions of the substrate 87, allowing for controlled heating and cooling of selected portions of the thermal transfer arrangement 82.

Figure 10:
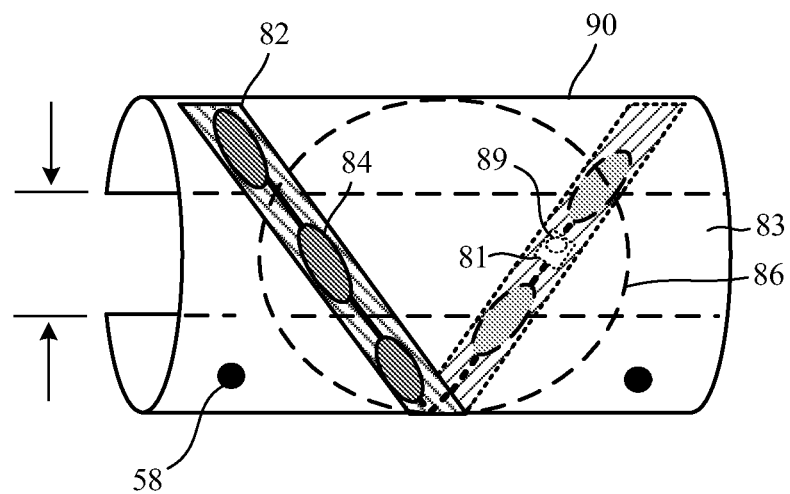
FIGS. 10 and 11 illustrate embodiments of an implantable extravascular apparatus comprising one or more thermoelectric elements configured to deliver denervation therapy and/or renal stimulation therapy to innervated renal vasculature in accordance with embodiments of the invention.
Figure 11:
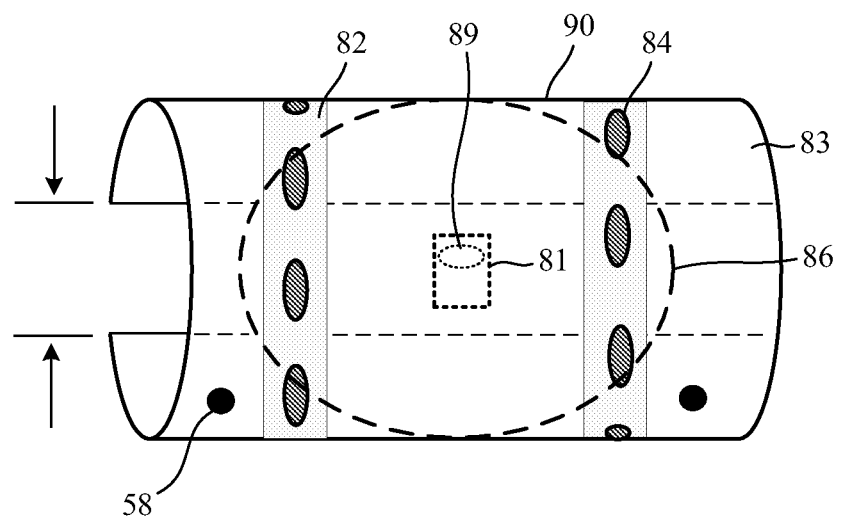

FIGS. 10 and 11 illustrate extravascular embodiments of a wireless implantable vascular apparatus 90 configured to deliver renal denervation therapy and/or stimulation therapy to control renal function. The embodiments shown in FIGS. 10 and 11 include a support structure 83 configured for deployment on an outer wall of the renal artery 12. The support structure 83 is preferably configured for chronic placement at the outer wall of the renal artery 12, and may be implemented as a cuff or clamp arrangement. A percutaneous intrathoracic access procedure, such as a laparoscopic, thoracoscopic, or other minimally invasive surgical procedure, is preferably used to place the wireless implantable vascular apparatus 90 on the outer wall of the renal artery 12.

The wireless implantable vascular apparatus 90 shown in FIGS. 10 and 11 comprise a thermal transfer arrangement 82 supported by the support structure 83 and includes one or more thermoelectric elements 84 configured to thermally couple to the outer wall of the renal artery 12. The thermoelectric elements 84 preferably comprise solid-state thermoelectric elements, such as Peltier elements. Although shown as comprising thermoelectric elements 84 in FIGS. 10 and 11, it is understood that the electrode arrangements of the intravascular renal artery apparatuses previously described with reference to FIGS. 5A-6C can be adapted for extravascular deployment on the support structure 83 shown in FIGS. 10 and 11.

The thermoelectric elements 84 are shown distributed on the surface of the support structure 83 in accordance with a predetermined pattern. In FIG. 10, a number of thermoelectric elements 84 are situated on the surface of the support structure 83 in accordance with a generally spiral or helical pattern. In FIG. 11, a number of thermoelectric elements 84 are situated on a substrate 87 that has a generally cylindrical shape that encircles the support structure 83. Two substrates 87 are shown for illustrative purposes in FIG. 11 with the thermoelectric elements 84 of the two substrates 87 arranged in a staggered configuration, such that at least a full revolution of renal artery wall tissue is subjected to treatment. It is understood that one or more than two substrates 87 may be employed. In some embodiments, some or all of the thermoelectric elements 84 may be thermally non-interactive with other thermoelectric elements 84 on the support structure 83. In other embodiments, some or all of the thermoelectric elements 84 may be thermally interactive with other thermoelectric elements 84 on the support structure 83.

The support structure 83 may incorporate a cuff mechanism that can be manipulated so that opposing edges of the cuff contact each other. Known cuff coupling mechanism may be used, such as a circumferential or annular cuff implementation. The support structure 83 may include other coupling mechanisms, such as a spiral or helical shaped coupling mechanism, among other configurations. The coupling mechanism may be integral to the support structure 83, such as by incorporation of an interlocking arrangement disposed along all or a portion of the opposing edges of the support structure 83 (e.g., a latching arrangement). A spiral or helical coupling arrangement may provide for in situ coupling of the support structure 83 to the outer wall of the renal artery 12, such as by wrapping a spiral or helical shape memory portion of the support structure 83 around the renal artery 12. Cuff embodiments in accordance with the present invention may be implemented to include features of various known vascular and nerve cuff structures, such as those disclosed in U.S. Pat. Nos. 7,584,004; 6,106,477; 5,251,634; and 4,649,936; and in U.S. Patent Publication No. 2008/0004673, which are incorporated herein by reference.

In FIGS. 7-11, each of the thermoelectric elements 84 is coupled to an electronics module 81 via a respective conductor 85. The electronics module 81 is supported by the support structure 83 and coupled to the thermal transfer arrangement 82 and an antenna arrangement 86, which is also supported by the support structure 83. The electronics module 81 preferably includes power circuitry configured to receive energy from a power source external of the wireless implantable apparatus, and preferably external of the renal artery 12, wirelessly via the antenna arrangement 86. The antenna arrangement 86 may include one or more antennae of varying configuration.

The antenna arrangement 86 shown in FIG. 7, for example, includes two loop antennae having a generally concentric shape that is supported by the support structure 83. The antenna arrangement 86 shown in FIGS. 8 and 9, by way of further example, includes one or more loop antennae having a generally oval shape that is supported by the support structure 83. In other embodiments, one, two, or more struts of the support structure 83 (e.g., struts of a stent) may be configured as antennae of the antenna arrangement 86.

The external power source may be implemented as power device 65 shown in FIGS. 5 and 6 or other power device described herein. For example, the power source may comprise a patient-external power source (e.g., a programmer, PC, portable communicator), an implantable power source (implantable medical device equipped with a battery or passive energy collector such as an inductive coil or other energy harvester), or both a patient-external power source and an implantable power source that operate cooperatively to supply energy to the wireless implantable vascular apparatus 80, 90.

In some embodiments, the thermoelectric elements 84 are configured or controlled to operate in a hyperthermic mode, and deliver thermal denervation therapy to the renal artery. In other embodiments, the thermoelectric elements 84 are configured or controlled to selectively operate in a hyperthermic mode, for thermally denervating the renal artery, and a hypothermic mode, for cooling endothelial and medial layer tissue. For example, the thermoelectric elements 84 may be configured or controlled to selectively operate in a hyperthermic mode and a hypothermic mode in a sequential manner or concurrently.

The electronics module 81 may incorporate a control circuit coupled to the power circuitry. The control circuit may include logic circuitry or a microprocessor configured to coordinate delivery of hypothermic ablation therapy to freeze renal nerves and terminate renal sympathetic nerve activity in a hypothermic mode of operation. The control circuit may be configured to coordinate delivery of hyperthermic therapy to at least heat renal nerves to above freezing, such as for delivering a sequence of freeze/thaw therapy cycles or a sequence of freeze/thaw/heat therapy cycles.

The control circuit may be configured to coordinate delivery of a hyperthermic ablation therapy to ablate renal nerves and terminate renal sympathetic nerve activity in a hyperthermic mode of operation. During a hyperthermic mode of operation, at least some elements or portion of the thermal transfer arrangement 82 may be operated in a hypothermic mode to provide cooling to the endothelium and media of the renal artery. The electronics module 81 may include or be coupled to one or more temperature sensors 89 which sense temperature at the thermal transfer arrangement 82 and/or the inner vessel wall of the renal artery 12.

As was previously described, temperature data acquired by the temperature sensor 89 is preferably communicated to the electronics module 81, via the antenna arrangement 86 or a separate antenna. The electronics module 81 transmits a signal that incorporates the temperature data to a device external of the renal artery 12, preferably in an encoded format. The temperature data is useful for controlling the operation of the implantable vascular apparatus 80, 90, such as by controlling the magnitude and duration of heat generation for one or both of renal denervation and renal stimulation procedures.

In some configurations, a first set of thermoelectric elements 84 is configured or controlled to operate in a hyperthermic mode, while another set of thermoelectric elements 84 is configured or controlled to operate in a hypothermic mode. In other configurations, all or a subset of the thermoelectric elements 84 are controlled to operate in a hyperthermic mode during a first duration of time, and then switch to operate in a hypothermic mode during a second duration of time. For example, the thermoelectric elements 84 can be driven to freeze renal nerves and ganglia in a hypothermic mode, and driven to generate and transfer heat to renal nerves and ganglia sufficient to kill renal nerves and ganglia in a hyperthermic mode Innervated and other renal vasculature may be subject to temperature cycling that involves transfer of thermal energy between the wireless implantable apparatus and renal tissue to achieve a desired freeze/thaw/heating profile.

Details of useful components and methodologies that can be adapted and incorporated in various embodiments of the invention are disclosed in commonly owned U.S. Pat. No. 7,238,184 and U.S. Patent Publication No. 2009/0024194, which are incorporated herein by reference. A detailed discussion of renal nerve structures and degrees of nerve disruption that can be achieved using embodiments of the invention is provided in commonly owned U.S. Provisional Application Ser. No. 61/291,476, filed Dec. 31, 2009 under which is incorporated herein by reference.

One or more physiologic parameters can be monitored during the renal denervation and renal stimulation procedures to determine the effect of these procedures on the patient's renal sympathetic nerve activity or renal function. For example, and as shown in FIGS. 5-11, an electrode arrangement 58 may be situated on the implantable vascular apparatus 50/60/80/90 to contact the inner or outer wall of the renal artery 12. The electrode arrangement 58 is preferably coupled to an electronics module 51/81 of the implantable vascular apparatus 50/60/80/90. The electrode arrangement 58 may incorporate one or multiple electrodes for sensing one or more physiologic parameters using either a unipolar or multipolar sensing configuration.

In some embodiments, the electrode arrangement 58 may be configured to measure nerve impulses transmitted along renal nerve fibers of the renal artery 12, including those that couple to or pass through the renal ganglion 24. By way of further example, one or more physiological parameters that are sensitive to changes in renal sympathetic nerve activity or renal function may be monitored using the electrode arrangement 58. The efficacy of the renal ablation may be determined based on measured changes in the physiological parameter(s).

Other sensors may be used alternatively or in addition to those of the electrode arrangement 58, which may include implantable or cutaneous (e.g., patient-external) sensors. For example, an impedance sensor and/or a pressure sensor may be used to monitor lung tissue impedance and/or blood pressure. Renal artery stimulation can be delivered and controlled automatically in response to physiologic sensors, such as lung tissue impedance and/or blood pressure measured using an impedance sensor and/or a pressure sensor. For example, the electrode arrangement 58 or other physiologic sensor may be used to sense ECG signals or a surrogate signal which is modulated by cardiac activity. Stimulation pulses to renal vasculature may be synchronized with the heart rhythm and pulse as part of renal stimulation therapy to control renal function.

Useful physiologic sensors that can be used in conjunction with an implantable vascular apparatus 50/60/80/90 for monitoring patient response to renal denervation and/or stimulation therapies and for automatically adjusting these therapies include sensors that measure nerve activity, cardiac electrical and/or mechanical activity (e.g., ECG, heart sounds), blood pressure, blood flow (e.g., flow or plethysmographic sensing), blood gas saturation (oxygen, carbon dioxide, etc.) via oximetry, blood chemistry, lung sounds, and impedance. Suitable apparatuses for these purposes are disclosed in commonly owned U.S. Patent Publication No. 2008/0234780 and in U.S. Patent Publication No. 2005/0192638, which are incorporated herein by reference.

Various sensors and monitoring processes may be implemented for purposes of detecting re-innervation of the renal artery following renal denervation. Renal nerve regeneration and re-innervation of the renal artery can occur weeks or months after renal denervation therapy as long as the endoneural tubes of the renal nerve fibers are intact. A chronically implanted vascular apparatus 50/60/80/90 in accordance with embodiments of the invention can be used to monitor for re-innervation of the renal artery following renal denervation.

One approach to monitoring for re-innervation of the renal artery involves monitoring for changes in a renal nerve activity signal during hypothermic stunning of renal nerves using sub-lethal cooling. An aspect of hypothermia on nerves is that the nerves may be stunned by sub-lethal cooling, recovering full function when cooling is terminated. By monitoring a renal nerve activity signal via electrodes, for example, changes of this signal during and after hypothermic stunning of renal vasculature can be detected. If sensed electrical activity decreases during stunning, it can be assumed that living nerves are nearby, indicating that re-innervation is occurring or has occurred and that additional renal denervation therapy is needed. It is noted that this monitoring approach may also be used for assessing the efficacy of a renal denervation therapy.

In some embodiments, a controller or processor of the implantable vascular apparatus 50/60/80/90 or other implantable or patient-external control device may be configured to coordinate monitoring of at least one physiologic parameter that facilitates detection of renal sympathetic nerve activity associated with re-innervation of the renal artery. Monitoring for renal sympathetic nerve activity associated with re-innervation of the renal artery can be conducted in a monitoring mode of the implantable vascular apparatus 50/60/80/90, in which hypothermic and/or hyperthermic therapy delivery is disabled.

Automatic or semi-automatic control of the renal artery stimulation and/or renal denervation may be effected by the electronics module 51/81 of the implantable vascular apparatus 50/60/80/90, by the controller of an external device 65, by an electronics module of an implantable device communicatively linked to the implantable vascular apparatus 50/60/80/90, or by a combination of two or more of these control resources.

Various components, devices, and methodologies that can be adapted for use in the context of various embodiments of the invention are disclosed in commonly owned U.S. Publication No. 2007/0260281 and 2009/0204170, each of which is incorporated herein by reference.

FIGS. 12-15 illustrate several embodiments of an implantable vascular apparatus 50/60/80/90 that receives energy wirelessly from an implantable or patient-external energy source in accordance with the invention. Although shown as comprising intravascular vascular apparatuses in FIGS. 12-15, it is understood that the extravascular renal apparatuses previously described with reference to FIGS. 10 and 11 may be used in the context of the embodiments shown in FIGS. 12-15, and that a combination of intravascular and extravascular renal apparatuses can be employed.

Figure 12:
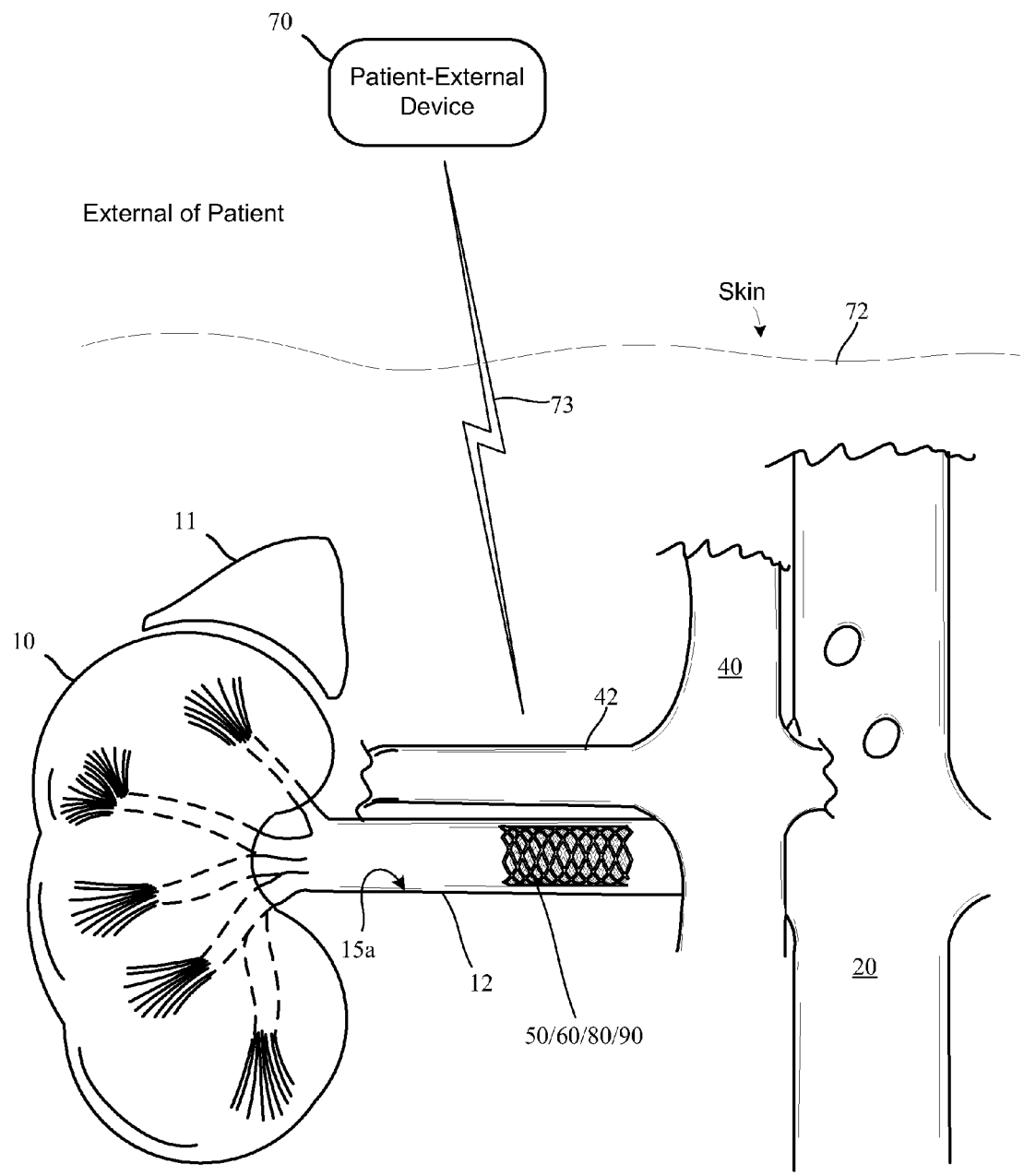
FIGS. 12-15 illustrate various embodiments of an implantable renal artery apparatus the receives energy wirelessly from an implantable or patient-external energy source for purposes of delivering one or both of renal denervation and stimulation therapy in accordance with embodiments of the invention.

FIG. 12 illustrates an embodiment that includes an implantable vascular apparatus 50/60/80/90 of a type previously described deployed chronically within a patient's renal artery 12. The implantable vascular apparatus 50/60/80/90 includes an inductive coil or an antenna that receives energy from a device 70 located external of the patient via a transcutaneous path through the skin 72.

In some embodiments, the patient-external device 70 is used to transfer energy sufficient to allow the implantable vascular apparatus 50/60/80/90 to deliver renal denervation therapy. The patient-external device 70 preferably includes an RF generator that generates an RF signal having a frequency typically in the range of 100 KHz to 10 MHz. The RF generator may be incorporated in or coupled to a processing device, such as a programmer, PC, or portable communicator.

Following renal denervation therapy, and assuming the patient is ambulatory thereafter, the patient may be provided a portable RF generator 70 in accordance with various embodiments. The portable RF generator 70 is configured to transfer energy transcutaneously to the implantable vascular apparatus 50/60/80/90. The energy transfer from the portable RF generator 70 and the implantable vascular apparatus 50/60/80/90 is sufficient to allow the implantable vascular apparatus 50/60/80/90 to deliver renal stimulation therapy to control renal function on a long-term ambulatory basis. A portable RF generator 70 may also be used in the embodiments shown in FIGS. 13-15.

The portable RF generator 70 preferably includes electronics for monitoring renal functions via one or more physiologic sensor of a type previously described, and for controlling stimulation energy to the renal artery 12. The portable RF generator 70 may also incorporate a communications interface that facilitates communications with a separate device or system, such as a programmer, medical system, PC, network server, wireless access point, cellphone, smartphone, or PDA. For example, the communications interface of the portable RF generator 70 may include one or both of a hardwire or wireless communication interface. Exemplary interfaces include USB; IEEE 1394 FireWire; Wi-Fi; cellular; Medical Implant Communication Service (MICS); Industrial, Scientific and Medical (ISM) radio band; and Short Range Devices (SRD) radio band, among others.

Figure 13:
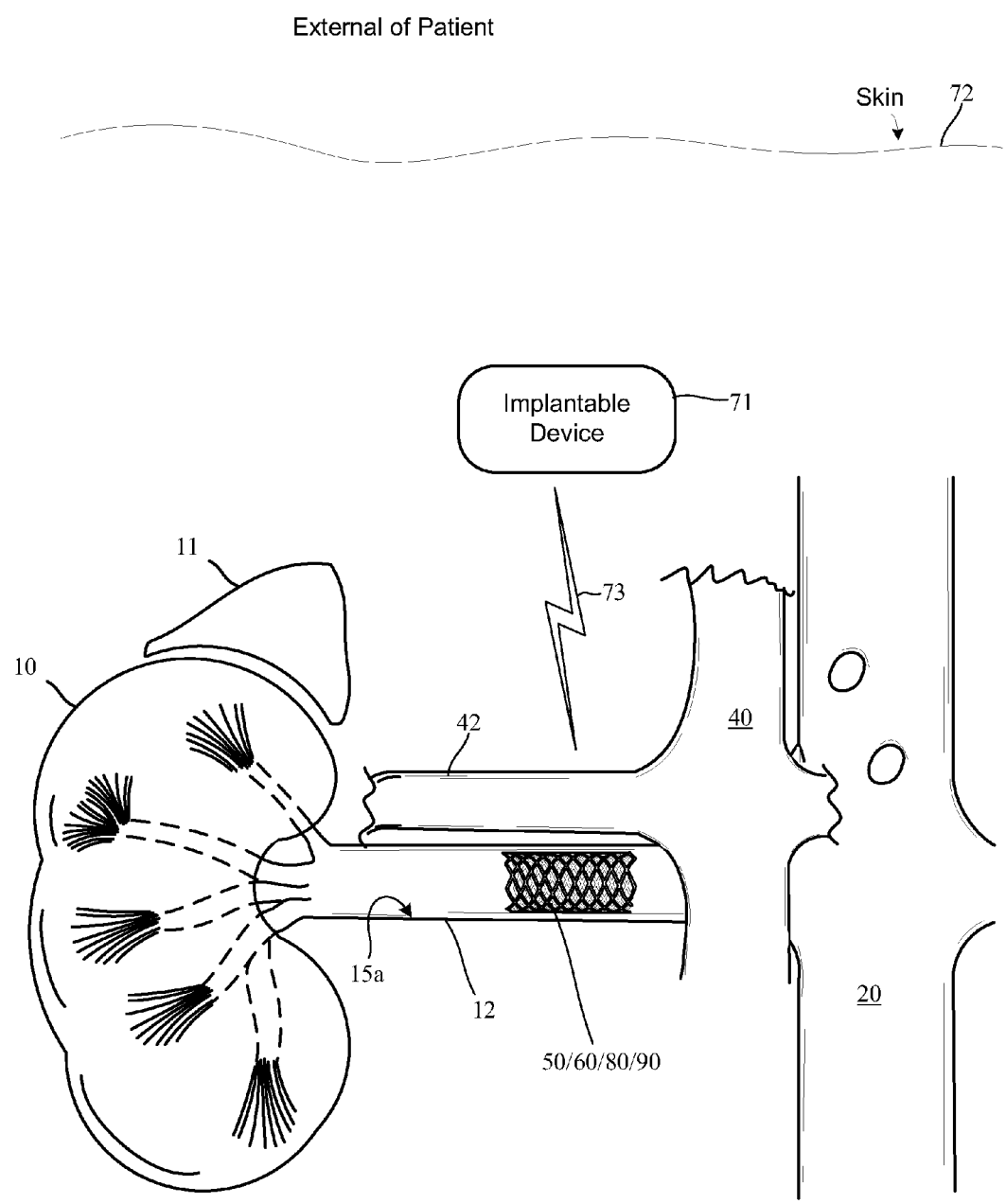

FIG. 13 illustrates an embodiment of an implantable vascular apparatus 50/60/80/90 the receives energy wirelessly from an implantable device 71. The implantable vascular apparatus 50/60/80/90 is of a type previously described and is shown deployed chronically within a patient's renal artery 12. The implantable vascular apparatus 50/60/80/90 includes an inductive coil or an antenna that receives energy from the implantable device 71, which is positioned within the patient's body below the skin 72. The implantable device 71 provides an in vivo power source for the implantable vascular apparatus 50/60/80/90. This power source may be a battery of an implantable medical device, such as an implantable stimulator, a cardiac rhythm management device such as a pacemaker, cardiac resynchronizer, or implantable cardioverter-defibrillator, a neurostimulation device, a drug pump, or other powered implantable apparatus. Alternatively, the implantable device 71 may comprise a battery and electronics that are dedicated to supplying wireless power and communications to the implantable vascular apparatus 50/60/80/90. The battery may be rechargeable from an external power transmitter.

Figure 14:
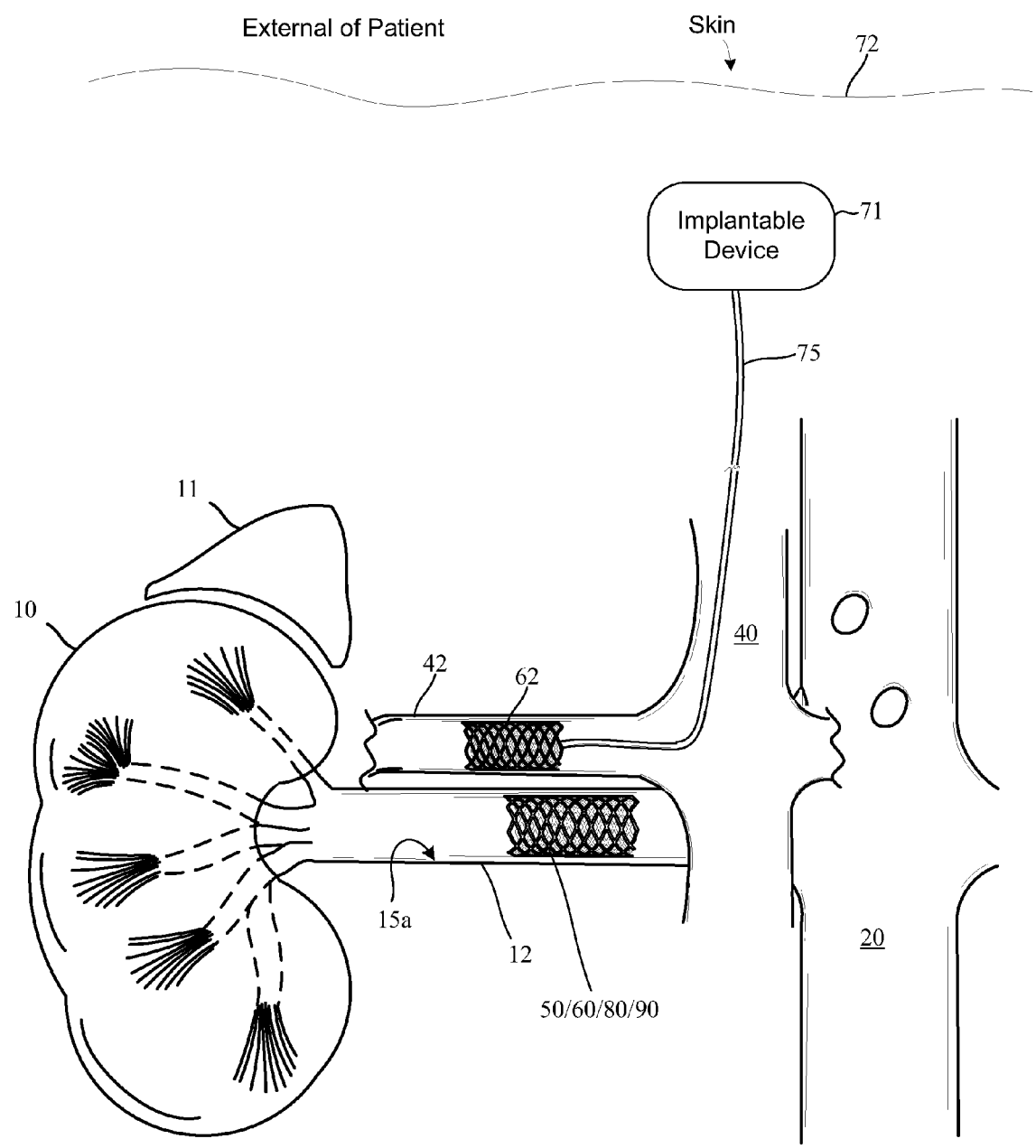
Figure 15:
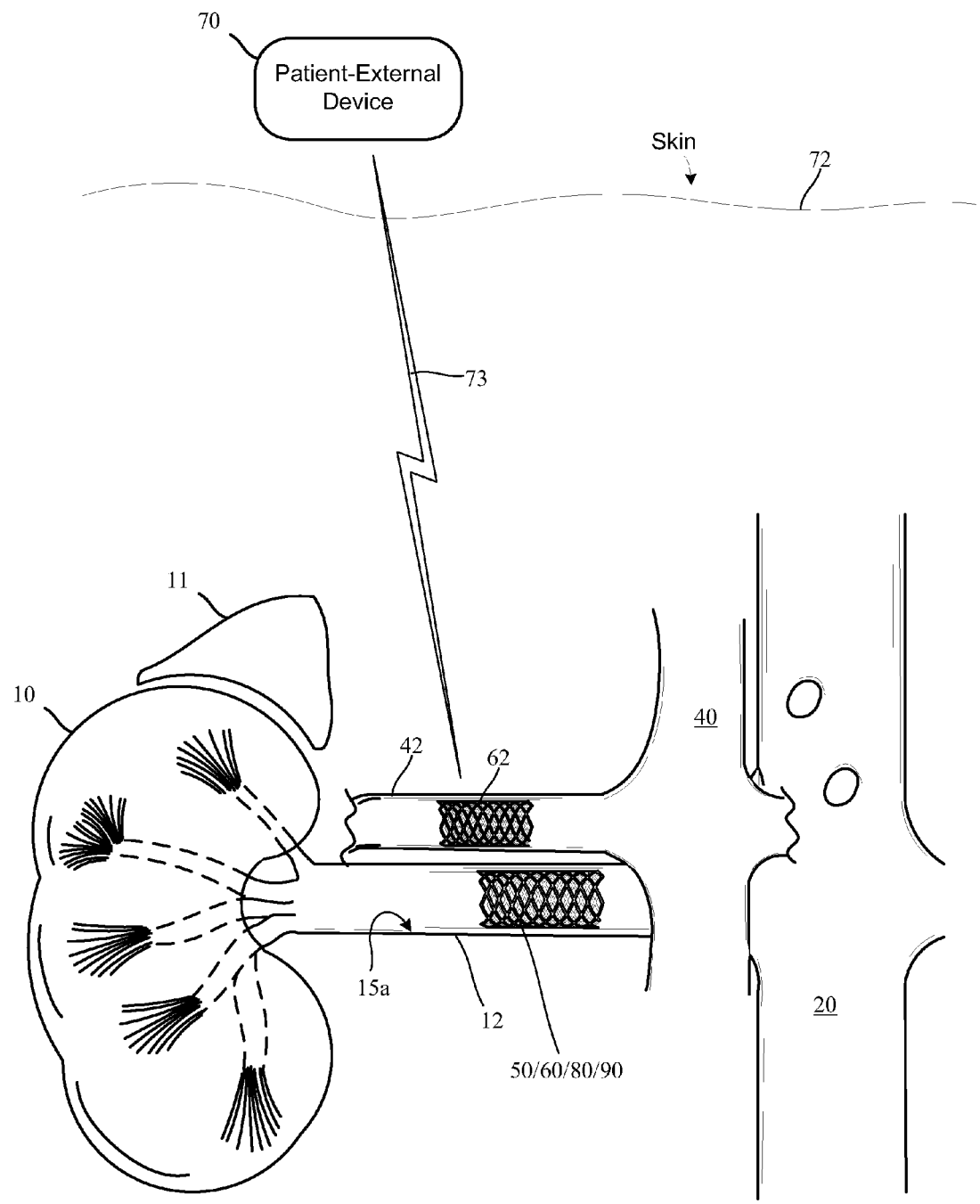

FIGS. 14 and 15 illustrate embodiments of an implantable vascular apparatus 50/60/80/90 configured to receive energy wirelessly from a separate intravascular or extravascular energy source 62 in accordance with the invention. Although vascular apparatuses 50/60/80/90 and 62 are shown as intravascular apparatuses in FIGS. 14 and 15, it is understood that the extravascular renal apparatuses previously described with reference to FIGS. 10 and 11 may be used in the context of the embodiments shown in FIGS. 14 and 15, and that a combination of intravascular and extravascular apparatuses can be employed.

In FIGS. 14 and 15, a transmit coil or antenna is provided on a source stent 62 configured for deployment in the renal vein 42. A receive stent 50/60/80/90 is configured for deployment in the adjacent renal artery 12. The source stent 62 supplies RF power using an RF transmit coil or antenna that is efficiently coupled to a receiver coil or antenna on the receive stent 50/60/80/90 via a transvenous path. In some embodiments, as is shown in FIG. 14, power is supplied to the source stent 62 from an implantable device 71, such as an implantable pulse generator, via a lead 75 that passes through the vena cava 40.

The implantable device 71 may include a pulse generator positioned in a pectoral pocket. Transmit coil current for the source stent 62 is supplied by the pulse generator via the lead 75. The pulse generator can contain multiple functions such as defibrillation and cardiac pacing. RF power is efficiently transmitted over the relatively short distance from the source stent 62 to the receive stent 50/60/80/90 in the renal artery 12. In other embodiments, as is shown in FIG. 15, power is supplied to the source stent 62 from a patient-external device 70, via a system-based or portable RF generator.

Anodes at the end of the receive stent 50/60/80/90 are configured to contact the renal artery wall 15*a* and to hyperpolarize the tissue and induce endothelium dependent vasodilation, as previously described. The anodes are insulated from the blood within the renal artery 12, while the cathode is positioned at the center of the receive stent 50/60/80/90 and is in contact with blood, but insulated from the renal artery wall 15*a*.

As was previously discussed, renal artery stimulation can occur automatically in response to physiologic sensors that measure, for example, lung tissue impedance and/or blood pressure. Renal artery stimulation can be initiated manually from a remote pulse generator controller, such as a programmer or portable communicator. In addition or in the alternative, ablation of the renal nerves and ganglia can be accomplished by inducing sufficiently large currents in renal artery tissue surrounding the receive stent electrodes using the pulse generator 71 or an external controller/transmitter 70. The ablation can be controlled by a temperature measurement made on the receive stent 50/60/80/90 and transmitted to the pulse generator 71 or patient-external controller/transmitter 70.

FIG. 16 is a schematic of a renal denervation and/or renal function control system in accordance with embodiments of the invention. FIG. 16 shows circuitry 200 of two primary apparatuses that are wirelessly linked together. The components of circuitry 200 and/or functions implemented by circuitry 200 may be distributed among an implantable source apparatus 62, an implantable receive apparatus 50/60/80/90, and an external RF generator in accordance with various embodiments. For example, and in accordance with some embodiments, only circuitry of the coil 208 shown in circuitry 220 is included in the implantable source apparatus 62, while the remaining components of circuitry 220 are included in a pulse generator or other implantable medical device which is coupled to the circuitry of coil 208. It is understood that at least some of the components of circuit 220 are included or otherwise coupled to the implantable source apparatus 62, and that some or all of the components of circuit 210 are included or otherwise coupled to the implantable receive apparatus 50/60/80/90.

The receive apparatus 50/60/80/90 is preferably configured for chronic fixation within a lumen of a renal artery 12 or on an outer wall of the renal artery 12. The source apparatus 62 is preferably configured for chronic fixation within a lumen of a renal vein 42 or on an outer wall of the renal vein 42 in proximity to the receive apparatus 50/60/80/90. The source apparatus 62 may also be located in or on the inferior vena cava 40 or elsewhere in the body in proximity to the receive apparatus 50/60/80/90. Preferably, the receive apparatus 50/60/80/90 is implemented using a stent. More preferably, the receive apparatus 50/60/80/90 and the source apparatus 62 are implemented using stents.

The transmitter electronics of the source apparatus 62 includes a microprocessor controlled switch 224/228 that creates pulsed current in a transmit antenna 206. Current is induced in a receive antenna 212 on the receive apparatus 50/60/80/90 and is rectified by rectifier 213 and stored on a capacitor 215. Denervation and/or stimulation energy output from the receive apparatus 50/60/80/90 is controlled by microprocessor 216. A DC current is delivered under the control of a microprocessor controlled switch 216/217 to the renal artery wall via an electrode arrangement 250, 260. Circuitry may be included, such as an H-bridge 263, to provide reverse polarity for charge neutralization.

Electrodes 250, 260 or other electrodes or sensors supported on or coupled to the receive apparatus 50/60/80/90 may be used to sense cardiac activity signals, such as ECG signals, through an amplifier 232 via conductor arrangement 233. In some embodiments, renal artery stimulation pulses may be synchronized with the heart rhythm and pulse, such as for renal function control therapies.

The circuitry 200 of the renal denervation and/or renal function control system shown in FIG. 16 is preferably used to controllably induce dilation of renal artery beds, but may also be used to induce dilation of artery beds other than those of the renal arteries, with or without ablation of the nerves. Ablation of the renal nerves and ganglia may be accomplished using the circuitry 200. For example, once implanted, an implantable power source (e.g., pulse generator) or a patient-external RF power source may be used to inject currents into the tissue adjacent the electrodes 250, 260 that are large enough to heat and ablate renal nerves and ganglia in or on the adventitia of the renal artery. A temperature sensor 207 of the receive circuit 210 may monitor the ablation temperature, and transmit this information to the control resource (e.g., programmer and/or operator) to control the ablation via the coil 212 or a separate antenna. As with all power and communication to the circuitry 200, the incoming energy is preferably encoded to prevent accidental stimulation from an external source.

The circuit 220 of the source apparatus 62 shown in FIG. 16 is configured as a controller/transmitter that can include a battery 226, a voltage regulator 225, and a microprocessor 224. As was discussed previously, power for the circuit 220 may be supplied by a battery of a subcutaneous medical device, such as an implantable pulse generator, stimulator, or monitor, typically positioned in a subcutaneous pocket. The inductive antenna 206 may be coupled via an electrical lead to the rest of the circuitry 220 contained in a subcutaneous medical device.

The microprocessor 224 of the source apparatus 62 may include an input-output (I/O) interface. A switch 228 can be coupled to the microprocessor 224 using the I/O interface, such as to control current flow from the battery 226 or an optional energy storage device, such as a capacitor 227, to an inductive antenna 206. In some embodiments, the inductive antenna 206 can include a wire loop inductor 208 (e.g., such as formed by multiple turns of fine wire, one or more traces or signal paths on a circuit board, or one or more other constructions). For example, the inductive antenna 206 can include multiple wire loops, at least some of which can be configured to be offset from each other or otherwise configured or arranged to generate two or more magnetic fields that can be spatially orthogonal to one another, such as to reduce orientation sensitivity of wireless energy transmission or wireless information communication using the inductive antenna 206.

A tuning element 229 can be included, such as to allow a range of frequencies to be selected at which magnetically-coupled energy 214 will be generated by the inductive antenna 206. The resulting inductance-capacitance (LC) circuit can form a resonant tank circuit, which can have an operable range of resonant frequencies selected from a range of 100 KHz to 10 MHz, but selected below the self-resonant frequency of the inductor 208 comprising the inductive antenna 206. Various embodiments of the tuning element 229 can include, but are not limited to, a capacitor, a variable-capacitance diode (e.g., "varicap" diode), an active circuit modeling a capacitor of a selected value, or the like. In some implementations, the switch 228 and the tuning element 229 can be replaced, such as by a combination of a voltage-controlled oscillator and power amplifier coupled to directly drive the inductive antenna 206, such as to generate the magnetically coupled energy 214 at a specified range of frequencies. The switch 228 can be implemented either mechanically, such as using a microminiature relay, or as solid-state device (e.g., FET, BJT, IGBT, SCR, thyristor, or the like).

In certain implementations, the regulator 225, the microprocessor 224, the sensing circuit 223, and the switch 228 can be co-integrated in a single integrated circuit or multi-chip module package. This microprocessor can include, among other elements, a microcontroller including one or more of a volatile or non-volatile memory, multiple input/output channels, an analog-to-digital converter, a power supply, a digital-to-analog converter, or one or more other circuits, modules, or components that, in an example, can be co-integrated in a single integrated circuit, a single circuit package, a multi-chip module package, a hybrid, a polyimide flex-circuit assembly, or the like.

In certain implementations, the initiation, timing, duration, or frequency range of the magnetically-coupled energy 214 can be controlled by the microprocessor 224, which can be provided with input from a sensing circuit 223. For example, the sensing circuit 223 can be coupled to one or more electrodes 205A, 205B in contact with renal artery wall tissue. The sensing circuit 223 can be coupled to one or more electrodes 204A, 204B in contact with or near cardiac tissue 202A. Sensing circuit 232 of the source circuit 220 can be configured to receive cardiac signals from one or more electrode or sensor arrangements 204A, 204B that couple to cardiac tissue or other body tissue useful for deriving cardiac activity information. For example, ECG signals can be coupled to the sensing circuit 232 and fed to the stimulus control logic 216 for synchronizing renal artery stimulation pulses with the heart rhythm and/or pulse, such as for renal function control therapies.

According to some embodiments, the source circuit 62 can be external to the body, and the electrodes 204A, 204B (and/or other electrodes) can be coupled to the skin of the patient (e.g., to measure an electrocardiogram). In other embodiments, the source circuit 62 can be included in an implantable cardiac rhythm management device, or one or more other implantable electronic units, that can include one or more sense electrodes 222A, 222B coupled to the sensing circuit 223. For example, one or more of the sense electrodes 222A, 222B can be disposed on the housing of the controller/transmitter 220. In another example, the controller/transmitter 220 can include an arrhythmia detector (such as using the microprocessor 224) configured to use information provided by the one or more sense electrodes 222A, 222B or other sensing information for detecting an arrhythmia. Sensing elements 232 and 233 may be used to sense physiologic information at the receiving apparatus 50/60/80/90, such as blood pressure in the renal artery, where this information is transmitted back to sensing element 223 through the wireless link 214B or a separate communication link. Such information can be used, for example, to control one or more wireless electrostimulation electrode assemblies 210, such as to provide coordinated electrostimulation to control or moderate renal functions for both left and right renal arteries 12 of a patient. The magnetically-coupled energy 214 can be generated for either or both wireless electrostimulation electrode assemblies 210 transferring the operating or electrostimulation energy 214A to the wireless electrostimulation electrode assembly 210, or information communication 214B with the wireless electrostimulation electrode assembly 210.

According to various embodiments, a first range of frequencies can be established for wireless energy transfer, and a second range of frequencies can be established for commanding the wireless electrostimulation electrode assembly 210 to deliver an electrostimulus. In the illustrative example shown in FIG. 16, a filter 209 can be configured to discriminate between the operating energy 214A and the information communication 214B. For example, the filter 209 can be configured to detect a particular range of frequencies included in the communication 214B captured by the wireless electrostimulation electrode assembly 210, such as by using an inductive pickup 212.

The filter 209 can be coupled to stimulus control logic 216. In certain embodiments, the logic 216 can be configured to inhibit or to initiate renal tissue electrostimulation, such as in response to the filter 209 detecting one or more specified signals. The filter 209 can include, in certain implementations, a band-pass filter, which can be coupled to a threshold comparator. In other implementations, the filter 209 can include a digital demodulator. For example, communication 214B can be encoded digitally and can include (or be transmitted concurrently to) operating energy 214A being wirelessly communicated to the wireless electrostimulation electrode assembly 210. Examples of digital encoding of communication 214B can include, but are not limited to, on-off keying, amplitude-shift keying, phase-shift keying, frequency-shift keying, or the like.

Various components, devices, and methodologies that can be adapted for use in the context of various embodiments of the invention are disclosed in commonly owned U.S. Publication No. 2009/0204170, which is previously incorporated herein by reference.

Figure 17:
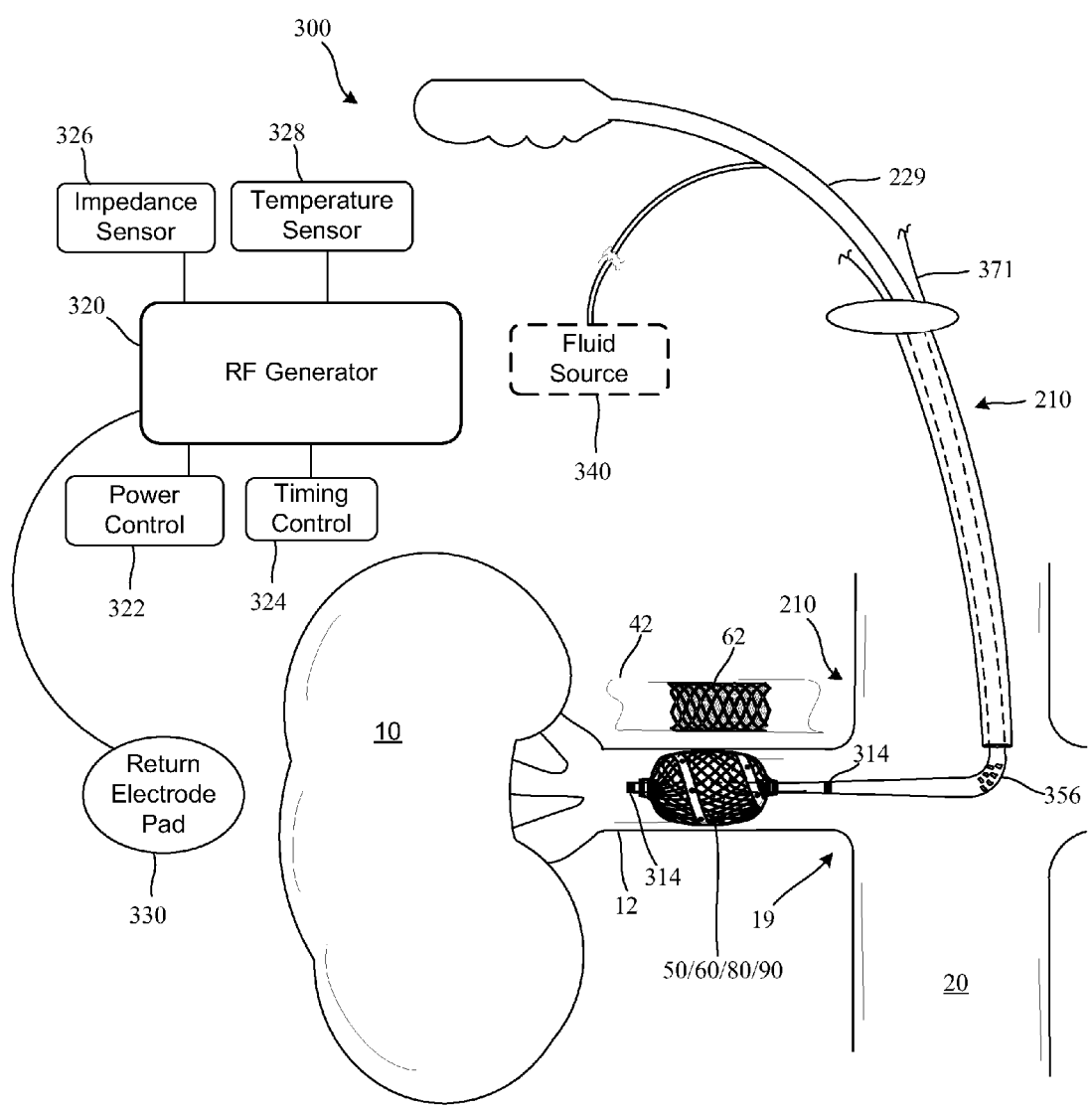
FIG. 17 shows a representative embodiment of an apparatus that can be used to implant a renal artery denervation and/or stimulation apparatus in accordance with the invention.

FIG. 17 shows a representative embodiment of an apparatus 300 that can be used to implant a renal artery denervation/stimulation apparatus 50/60/80/90 in accordance with the invention. The apparatus 300 can also be used to implant a renal vein source apparatus 62 in accordance with embodiments of the invention. According to embodiments that employ an implantable medical device having a battery (e.g., pulse generator), the battery can be connected to the renal vein source apparatus 62 via an electrical lead. After implanting one or both of the renal artery denervation/stimulation apparatus 50/60/80/90 and renal vein source apparatus 62, the apparatus 300 can be removed from the patient's body.

According to various embodiments, the apparatus 300 illustrated in FIG. 17 includes an RF generator 320 which is shown to include power control circuitry 322 and timing control circuitry 324. The RF generator 320 is also shown to include an impedance sensor 326 (optional) and temperature measuring circuitry 328. The impedance sensor 326 and temperature measuring circuitry 328 are respectively coupled to impedance and temperature sensors of the renal artery denervation/stimulation apparatus 50/60/80/90.

The RF generator 320 may include a return pad electrode 330 that is configured to comfortably engage the patient's back or other portion of the body near the kidneys for operating in a monopolar mode. According to embodiments that do not include a renal vein source apparatus 62, RF energy produced by the RF generator 320 is coupled to the renal artery denervation/stimulation apparatus 50/60/80/90 or to an implantable device equipped with a receiver for receiving the RF energy and a transmitter for transmitting energy wirelessly to the renal artery denervation/stimulation apparatus 50/60/80/90. In some embodiments that include a renal vein source apparatus 62, RF energy produced by the RF generator 320 can be coupled to the renal vein source apparatus 62, and renal vein source apparatus 62 wirelessly transmits energy to the renal artery denervation/stimulation apparatus 50/60/80/90.

It is understood that the RF generator system shown in FIG. 17 as a patient-external system may instead be incorporated in an implantable system as previously discussed. The implantable system may receive RF energy from a patient-external source, and energy received and/or stored by the implantable system may be transmitted to the renal vein source apparatus 62 via the RF generator 320 or via an electrical lead. The source apparatus 62 supplies energy received from the RF generator 320 or the electrical lead to the renal artery denervation/stimulation apparatus 50/60/80/90.

In general, when renal artery tissue temperatures rise above about 113° F. (50° C.), protein is permanently damaged (including those of renal nerve fibers). For example, any mammalian tissue that is heated above about 50° C. for even 1 second is killed. If heated over about 65° C., collagen denatures and tissue shrinks If heated over about 65° C. and up to 100° C., cell walls break and oil separates from water. Above about 100° C., tissue desiccates.

Temperature sensors incorporated into the renal artery denervation/stimulation apparatus 50/60/80/90 allow continuous monitoring of renal artery tissue temperatures, and RF generator power is automatically adjusted so that the target temperatures are achieved and maintained. An impedance sensor arrangement 326 may be used to measure and monitor electrical impedance during RF denervation therapy, and the power and timing of the RF generator 320 may be moderated based on the impedance measurements.

Depending on the power applied, duration of time the energy is applied to renal vasculature, and the resistance of renal artery tissues, temperature decreases rapidly with distance from the renal artery denervation/stimulation apparatus 50/60/80/90, limiting lesion size and extent of damage to neighboring tissues. The size of the ablated area is determined largely by the size and shape of the conductive element(s) of the renal artery denervation/stimulation apparatus 50/60/80/90, the power applied, and the duration of time the energy is applied.

In accordance with embodiments for performing renal denervation using a percutaneous access system followed by chronic implant of a renal artery denervation/stimulation apparatus 50/60/80/90, the apparatus 300 of FIG. 17 may include a fluid source 340 containing a coolant or a cryogen. The coolant or cryogen may be communicated from the fluid source 340 to a location proximate the renal artery denervation/stimulation apparatus 50/60/80/90 for cooling the renal artery wall during denervation. For example, the apparatus 300 can be used to deliver a cryocatheter or cryoballoon for deployment within a void of the renal artery denervation/stimulation apparatus 50/60/80/90.

Marker bands 314 can be placed on one or multiple parts of the catheter apparatus 210, 229, 371 to enable visualization during implant procedures. For example, one or more portions of the catheter 229, such as the hinge mechanism 356, may include a marker band 314. The marker bands 314 may be solid or split bands of platinum or other radiopaque metal, for example.

The hinge mechanism 356 shown in FIG. 17 may be constructed to enhance user manipulation of the catheter 229 when navigating around a nearly 90 degree turn from the abdominal aorta into the renal artery. It is understood that one or more hinge mechanisms 356 may be built into other catheters and sheaths that may be used to facilitate access to the renal artery via the abdominal aorta.

The shaft of the catheter 229 may be formed to include an elongate core member and a tubular member disposed about a portion of the core member. The tubular member may have a plurality of slots formed therein. The slotted hinge region 356 of the catheter's shaft may be configured to have a preferential bending direction. Details of useful hinge arrangements that can be incorporated into embodiments of a catheter 229 of the invention or other component that facilitates access to the renal artery/vein from the abdominal aorta/inferior vena cava are disclosed in U.S. Patent Publication Nos. 2008/0021408 and 2009/0043372, which are incorporated herein by reference. It is noted that the catheter 229 may incorporate a steering mechanism in addition to, or exclusion of, a hinge arrangement 356. Known steering mechanisms incorporated into steerable guide catheters may be incorporated in various embodiments of a catheter 229 of the present invention.

The discussion provided herein concerning degrees of induced renal nerve damage, temperature ranges, amount of energy delivered into target tissue, and other embodiment details presented in this disclosure are provided for non-limiting illustrative purposes. Actual therapeutic parameters associated with the denervation and renal stimulation apparatuses and methodologies may vary somewhat or significantly from those described herein, and be impacted by a number of factors, including patient-specific factors (e.g., the patient's unique renal vasculature and sympathetic nervous system characteristics), refractoriness to drugs impacting renal function, type and technology of the therapy device(s), therapy duration and frequency, use of a single therapy device or multiplicity of therapy devices (in sequential or concurrent use), structural characteristics of the therapy device(s) employed, and other implementation and physiologic particulars, among others.

The foregoing description of the various embodiments of the invention has been presented for the purposes of illustration and description. It is not intended to be exhaustive or to limit the invention to the precise form disclosed. Many modifications and variations are possible in light of the above teaching. For example, the devices and techniques disclosed herein may be employed in vasculature of the body other than renal vasculature, such as coronary and peripheral vessels and structures. It is intended that the scope of the invention be limited not by this detailed description, but rather by the claims appended hereto.

What is claimed is:

1. An apparatus for intravascular delivery of a therapy to a first vessel of a patient, comprising:
   a stent dimensioned for deployment within the first vessel, the stent adapted for chronic fixation within the first vessel;
   a controller supported by the stent;
   an electrode arrangement supported by the stent;
   an antenna arrangement supported by the stent and electrically coupled to the electrode arrangement, the antenna arrangement configured to receive energy from a power source external of the first vessel;
   the electrode and antenna arrangements operative in at least one of:
      an ablation configuration that produces current densities sufficient to ablate target tissue at or proximate the vessel; and
      a stimulation configuration that produces current densities sufficient to induce endothelium dependent vasodilation of a first vessel bed;
   wherein the power source supplies energy to the antenna arrangement other than by way of a percutaneous electrical lead for at least the stimulation configuration.

2. The apparatus of claim 1, wherein the electrode and antenna arrangements are selectively operative in the ablation configuration and the stimulation configuration.

3. The apparatus of claim 1, wherein the electrode arrangement comprises:
   an anode contact arranged to electrically couple to an inner wall of the first vessel and electrically insulated from blood passing through a lumen of the stent; and
   a cathode contact arranged to electrically couple with blood passing through the lumen of the stent and electrically insulated from the inner wall of the first vessel.

4. The apparatus of claim 1, wherein the power source comprises a power source external of the patient or an implantable power source.

5. The apparatus of claim 1, wherein the power source supplies energy to the antenna arrangement by way of the percutaneous electrical lead in the ablation configuration.

6. The apparatus of claim 1, wherein the power source comprises a power source configured to wirelessly couple energy to the antenna arrangement.

7. The apparatus of claim 1, wherein the power source comprises:
   an implantable structure configured for deployment within a second vessel at a vessel location proximate a location of the stent; and
   a transmitter supported by the implantable structure and configured to transmit energy to the antenna arrangement via a transvascular pathway.

8. The apparatus of claim 1, wherein the stent comprises at least two struts, and the antenna arrangement comprises the at least two struts.

9. The apparatus of claim 1, comprising circuitry coupled to the antenna and electrode arrangements, the circuitry configured to receive current induced in the antenna arrangement and store a charge developed using the induced current.

10. The apparatus of claim 1, comprising a sensing circuit configured for sensing cardiac activity and supported by the stent, the controller configured to transmit stimulation pulses to the first vessel wall via the electrode arrangement in synchrony with sensed cardiac events.

11. The apparatus of claim 1, wherein the electrode and antenna arrangements, in the stimulation configuration, are configured to produce current densities sufficient to hyperpolarize endothelium adjacent the stent and cause production and release of nitric oxide into blood flowing past the stent, the amount of released nitric oxide sufficient to cause vasodilation of the first vessel bed distal to the stent.

12. The apparatus of claim 1, wherein the apparatus is configured ablate innervated renal nerve tissue at or proximate a renal artery.

13. The apparatus of claim 11, wherein the apparatus is configured to deliver repeated renal nerve ablation in response to detection of re-innervation of the renal artery.

14. The apparatus of claim 12, comprising a sensor configured for sensing a physiologic parameter that facilitates detection of renal sympathetic nerve activity associated with re-innervation of the vessel.

15. An apparatus for intravascular delivery of a therapy to a vessel of a patient, comprising:
a stent dimensioned for deployment within the vessel, the stent adapted for chronic fixation within the vessel;
a controller supported by the stent;
a sensing circuit for sensing cardiac activity support by the stent;
an electrode arrangement supported by the stent;
an antenna arrangement supported by the stent and electrically coupled to the electrode arrangement, the antenna arrangement configured to receive energy from a power source external of the vessel;
the electrode and antenna arrangements operative in at least one of:
an ablation configuration that produces current densities sufficient to ablate target tissue at or proximate the vessel; and
a stimulation configuration that produces current densities sufficient to induce endothelium dependent vasodilation of a vessel bed;
wherein the power source supplies energy to the antenna arrangement other than by way of a percutaneous electrical lead for at least the stimulation configuration; and
wherein the apparatus is configured to deliver repeated ablation in response to detection of re-innervation of the vessel.

16. The apparatus of claim 14, comprising circuitry coupled to the antenna and electrode arrangements, the circuitry configured to receive current induced in the antenna arrangement and store a charge developed using the induced current.

17. The apparatus of claim 14, wherein the electrode arrangement comprises:
an anode contact arranged to electrically couple to an inner wall of the vessel and electrically insulated from blood passing through a lumen of the stent; and
a cathode contact arranged to electrically couple with blood passing through the lumen of the stent and electrically insulated from the inner wall of the vessel.

18. A method for delivering of a therapy to a vessel of a patient, comprising:
receiving energy by an antenna arrangement supported by a stent adapted for chronic fixation within the vessel from a power source external of the vessel;
communicating the energy received by the antenna arrangement to an electrode arrangement supported by the stent;
controlling a transmission of energy to the electrode arrangement in synchrony with sensed cardiac events; and
operating the electrode and antenna arrangements in at least one of:
an ablation configuration for producing current densities sufficient to ablate target tissue at or proximate the vessel; and
a stimulation configuration for producing current densities sufficient to induce endothelium dependent vasodilation of a vessel bed;
wherein the power source supplies energy to the antenna arrangement other than by way of a percutaneous electrical lead for at least the stimulation configuration.

19. The method of claim 17, further comprising selectively operating the electrode and antenna arrangements in the ablation configuration and the stimulation configuration.

20. The method of claim 17, wherein the ablation configuration is capable of delivering repeated ablation in response to detection of a physiologic parameter.

* * * * *